(12) United States Patent
Kato et al.

(10) Patent No.: US 7,132,546 B2
(45) Date of Patent: Nov. 7, 2006

(54) ANILINE DERIVATIVES OR SALTS THEREOF AND CYTOKINE PRODUCTION INHIBITORS CONTAINING THE SAME

(75) Inventors: Fuminori Kato, Shiga (JP); Hirohiko Kimura, Shiga (JP); Shunji Yuki, Shiga (JP); Kazuhiro Yamamoto, Shiga (JP); Takashi Okada, Shiga (JP)

(73) Assignee: Ishihara Sangyo Kaisha, Ltd., Osaka (JP)

(*) Notice: Subject to any disclaimer, the term of this patent is extended or adjusted under 35 U.S.C. 154(b) by 79 days.

(21) Appl. No.: 10/451,101

(22) PCT Filed: Dec. 21, 2001

(86) PCT No.: PCT/JP01/11282

§ 371 (c)(1),
(2), (4) Date: Jun. 19, 2003

(87) PCT Pub. No.: WO02/051397

PCT Pub. Date: Jul. 4, 2002

(65) Prior Publication Data

US 2004/0048891 A1 Mar. 11, 2004

(30) Foreign Application Priority Data

Dec. 22, 2000 (JP) .............................. 2000-391175

(51) Int. Cl.
*C07D 213/64* (2006.01)
(52) U.S. Cl. ...................... 546/300; 546/288; 546/304; 546/307; 546/312
(58) Field of Classification Search ................ 546/300, 546/312; 514/312
See application file for complete search history.

(56) References Cited

U.S. PATENT DOCUMENTS 5,081,125 A * 1/1992 Maienfisch et al. ......... 514/269

FOREIGN PATENT DOCUMENTS

| CA | 2 407 587 | 11/2001 |
|---|---|---|
| EP | 1024138 | 8/2000 |
| JP | 10-251144 | 9/1998 |
| WO | 95/00146 | 1/1995 |
| WO | 98/27058 | 6/1998 |
| WO | 98/27081 | 6/1998 |
| WO | 99/15164 | 4/1999 |
| WO | 99/51580 | 10/1999 |
| WO | 00/40235 | 7/2000 |
| WO | 00/40239 | 7/2000 |
| WO | 01/83427 | 11/2001 |

OTHER PUBLICATIONS

Steven W. Djuric et al.: "3,5-bis(trifluoromethyl) pyrazols: A novel class of NFAT transcription factor regulator" Journal of Medicinal Chemistry, vol. 43, No. 16, pp. 2975-2981 Sep. 2000.
Satoru Niwa et al.: "Effect of Am-80, a retinoid derivative, on 2, 4-dinitrofluorobenzene-induced contact dermatitis in mice" Pharmacology, vol. 60, No. 4, pp. 208-214 Jun. 2000.
David L. Selwood, et al., "Structure-Activity Relationships of Antifilarial Antimycin Analogues: Multivariate Pattern Recognition Study", Journal of Medicinal Chemistry, vol. 33, No. 1, XP-002071789, 1990, pp. 136-142.

* cited by examiner

*Primary Examiner*—Patricia L. Morris
(74) *Attorney, Agent, or Firm*—Oblon, Spivak, McClelland, Maier & Neustadt, P.C.

(57) ABSTRACT

The present invention provides a cytokine production inhibitor containing as an active ingredient an aniline derivative of the formula (I) or a salt thereof:

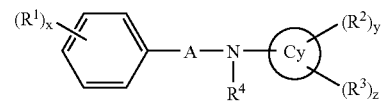

[wherein A is CO or $SO_2$; Cy is an aryl group or a heterocyclic group; each of $R^1$ and $R^2$ which are independent of each other, is a halogen atom, a cyano group, a nitro group, an alkyl group which may be substituted, an alkenyl group which may be substituted, an alkynyl group which may be substituted, a cycloalkyl group which may be substituted, a cycloalkenyl group which may be substituted, an aryl group which may be substituted, a heterocyclic group which may be substituted, an amino group which may be substituted or a —B-Q group; $R^3$ is a -$M^1$-$M^2$-$R^5$ group; $R^4$ is a hydrogen atom or an alkyl group which may be substituted; x is an integer of from 0 to 5; y is an integer of from 0 to 4; and z is an integer of from 0 to 1].

5 Claims, No Drawings

ANILINE DERIVATIVES OR SALTS THEREOF AND CYTOKINE PRODUCTION INHIBITORS CONTAINING THE SAME

TECHNICAL FIELD

The present invention relates to aniline derivatives or salts thereof, and cytokine production inhibitors containing the same as an active ingredient. The cytokine production inhibitors of the present invention are useful as preventive or therapeutic medicines for diseases accompanied by hyperactivated immune functions, such as allergic diseases, systemic autoimmune diseases and organ specific autoimmune diseases, or as preventive or therapeutic medicines for graft rejection in organ transplantation.

BACKGROUND ART

In immune reactions in the body, cytokines produced from various immunocytes control direction of the immune responses. In this regulation of immune responses, it is helper T cells that play a central role, and they are classified into subsets Th1 and Th2 depending upon the type of cytokines they produce. Th1 type cells are known to produce mainly e.g. interleukin 2 (IL-2) and interferon γ (IFN-γ) and to be concerned with cellular immunity such as protection of infection against e.g. virus and bacteria. Th2 type cells are known to produce mainly e.g. interleukin 4 (IL-4), interleukin 5 (IL-5), interleukin 6 (IL-6), interleukin 10 (IL-10) and interleukin 13 (IL-13) and to be concerned with humoral immunity such as protection of infection against parasites and antibody production from B cells. However, it has been clarified that if control of such biophylactic mechanism dysfunctions or deteriorates for some reason, hyperactivation or imbalance of immune function may occur, thus inducing or deteriorating various diseases.

Immune response of Th2 type induces or activates, due to its hyperactivation, allergic inflammation reactions such as immediate type allergy with which IgE antibody or mast cells are mainly concerned, and delayed-type allergy with which eosinophils are mainly concerned, and is deeply concerned with induction or deterioration of various allergic diseases such as urticaria, food allergy, anaphylactic shock, hypereosinophilic syndrome, asthma, allergic rhinitis, allergic conjunctivitis and atopic dermatitis. Further, abnormal hyperactivation of immune reaction of Th2 type is deeply concerned also with systemic autoimmune diseases in a pathophysiologic state where antibody production or humoral immunity is hyperactivated, such as systemic lupus erythematosus. It is considered to be important to control the immune response of Th2 type in order to treat or prevent such allergic diseases. On the other hand, immune response of Th1 type induces or activates cellular immune responses due to its hyperactivation, and is deeply concerned with induction or deterioration of organ specific autoimmune diseases such as chronic rheumatoid arthritis, type I diabetes, Hashimoto's thyroiditis, myasthenia gravis and multiple sclerosis. Further, cellular immune response of Th1 type is deeply concerned also with graft rejection accompanying organ transplantation. It is considered to be important to control immune response of Th1 type in order to prevent or treat such autoimmune diseases or graft rejection after transplantation.

As compounds which are analogous in chemical structures to the aniline derivative or a salt thereof as an active ingredient of the cytokine production inhibitors of the present invention, compounds as disclosed in WO95/146, WO98/27081, WO98/27058, WO99/15164, WO99/51580 and WO00/40235 may, for example, be mentioned. However, such compounds and the compounds of the present invention are different in their chemical structures.

At the present time, it is difficult to treat such serious immune or allergic diseases by specifically regulating immune response of Th1 or Th2 type, and immunosuppressant agents which strongly suppress production of both Th1 and Th2 type cytokines, such as cyclosporin and FK506, in addition to steroids, are mainly used as therapeutic medicines for such diseases. However, various side effects such as dysfunction of adrenal cortex, diabetes, peptic ulcer and glaucoma have been problematic with respect to steroids, and serious side effects such as damages in kidney and central nervous system have been problematic with respect to cyclosporin and FK506, and development of a new type of cytokine production inhibitors which are different from the above agents, has been desired.

DISCLOSURE OF THE INVENTION

The present inventors have found that aniline derivatives having chemical structures which are totally different from those of active ingredients in existing agents have cytokine production inhibitory effects, and the present invention has been accomplished on the basis of this discovery. The aniline derivatives suppress production of Th2 type cytokine, whereby they are useful as preventive or therapeutic medicines for various allergic diseases such as urticaria, food allergy, anaphylactic shock, hypereosinophilic syndrome, asthma, allergic rhinitis, allergic conjunctivitis and atopic dermatitis; and systemic autoimmune diseases in which antibody production or humoral immunity is hyperactivated, such as systemic lupus erythematosus. Further, they suppress production of Th1 type cytokine, whereby they are useful as preventive or therapeutic medicines for organ specific autoimmune diseases such as chronic rheumatoid arthritis, type I diabetes, Hashimoto's thyroiditis, myasthenia gravis and multiple sclerosis; and graft rejection accompanying organ transplantation.

The present inventors have conducted extensive studies to find more excellent cytokine production inhibitors and as a result, have accomplished the present invention. Namely, the present invention relates to a cytokine production inhibitor containing as an active ingredient an aniline derivative of the formula (I) or a salt thereof:

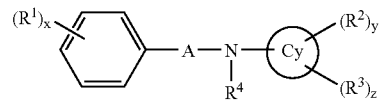

[wherein A is CO or $SO_2$; Cy is an aryl group or a heterocyclic group; each of $R^1$ and $R^2$ which are independent of each other, is a halogen atom, a cyano group, a nitro group, an alkyl group which may be substituted, an alkenyl group which may be substituted, an alkynyl group which may be substituted, a cycloalkyl group which may be substituted, a cycloalkenyl group which may be substituted, an aryl group which may be substituted, a heterocyclic group which may be substituted, an amino group which may be substituted or a —B-Q group (wherein B is O, CO, COO, OCO, S, SO or $SO_2$; and Q is a hydrogen atom, an alkyl group which may be substituted, an alkenyl group which may be substituted, an alkynyl group which may be substituted, a cycloalkyl group which may be substituted, a cycloalkenyl group which may be substituted, an aryl group which may be substituted, a heterocyclic group which may be substituted or an amino group which may be substituted); $R^3$ is a $-M^1-M^2-R^5$ group {wherein each of $M^1$ and $M^2$ which are independent of each other, is O, S, a $NR^6$ group (wherein $R^6$ is a hydrogen atom or an alkyl group which may be substituted), a single bond, a $C_{1-2}$ alkylene chain, CO, SO or $SO_2$, or $M^1$ and $M^2$ together may form —N═N—; and $R^5$ is a cycloalkyl group which may be substituted, an aryl group which may be substituted or a heterocyclic group which may be substituted}; $R^4$ is a hydrogen atom or an alkyl group which may be substituted; x is an integer of from 0 to 5; y is an integer of from 0 to 4; and z is an integer of from 0 to 1; provided that (1) a case where Cy is a phenyl group, and the substituent at the 4-position of the phenyl group is a pyrazole group which may be substituted or a triazole group which may be substituted, and (2) a case where Cy is a phenyl group, the substituent at the 2-position of the phenyl group is an alkyl group, and the substituent at the 5-position is a —NHCO—$(CH_2)$q-R group (wherein q is an integer of from 1 to 4, and R is an aryl group or a cycloalkyl group) are excluded].

The salt of the aniline derivative of the above formula (I) may be any pharmaceutically acceptable salt, and it may, for example, be a mineral acid salt such as a hydrochloride, a sulfate or a nitrate; an organic acid salt such as a p-toluene sulfonate, a propane sulfonate or a methane sulfonate; an alkali metal salt such as a potassium salt or a sodium salt; an alkaline earth metal salt such as a calcium salt; or an organic amine salt such as a triethanol amine salt or a tris(hydroxymethyl)aminomethane salt. Some of these salts have crystal water.

Each of the alkyl group which may be substituted represented by each of $R^1$, $R^2$, $R^4$, $R^6$ and Q, and the alkyl moiety in each of the secondary substituent and the tertiary substituent as described hereinafter, may be usually one having a carbon number of from 1 to 18, and it may, for example, be a methyl group, an ethyl group, a propyl group, a butyl group, a pentyl group, a hexyl group, a heptyl group, an octyl group, a decyl group or a nonadecyl group, and they include linear or branched aliphatic structural isomers.

Each of the alkenyl group which may be substituted represented by each of $R^1$, $R^2$ and Q, and the alkenyl moiety in each of the secondary substituent and the tertiary substituent as described hereinafter, may be usually one having a carbon number of from 2 to 18, and it may, for example, be a vinyl group, a propenyl group, a butenyl group, a pentenyl group, a hexenyl group, a decenyl group or a nonadecenyl group, and they include linear or branched aliphatic structural isomers.

Each of the alkynyl group which may be substituted represented by each of $R^1$, $R^2$ and Q, and the alkynyl moiety in each of the secondary substituent and the tertiary substituent as described hereinafter, may be usually one having a carbon number of from 2 to 18, and it may, for example, be an ethynyl group, a propynyl group, a butynyl group, a pentynyl group, a hexynyl group, a decynyl group or a nonadecynyl group, and they include linear or branched aliphatic structural isomers.

Each of the cycloalkyl group which may be substituted represented by each of $R^1$, $R^2$, $R^5$ and Q and the cycloalkyl moiety in each of the secondary substituent and the tertiary substituent as described hereinafter, may be usually one having a carbon number of from 3 to 10, and it may, for example, be a monocyclic group such as a cyclopropyl group, a cyclobutyl group, a cyclopentyl group, a cyclohexyl group or a cyclooctyl group; a fused-polycyclic group; or a crosslinked polycyclic group such as an adamantyl group, a noradamantyl group, a norbornanyl group or a norbornanonyl group.

Each of the cycloalkenyl group which may be substituted represented by each of $R^1$, $R^2$ and Q and the cycloalkenyl moiety in each of the secondary substituent and the tertiary substituent as described hereinafter, may be usually one having a carbon number of from 3 to 10, and it may, for example, be a monocyclic group such as a cyclopentenyl group, a cyclohexenyl group or a cyclooctenyl group, a fused-polycyclic group or a crosslinked polycyclic group.

Each of the aryl group which may be substituted represented by each of $R^1$, $R^2$, $R^5$ and Q, the aryl group represented by Cy and the aryl moiety in each of the secondary substituent and the tertiary substituent as described hereinafter, may be a fused-polycyclic group such as a naphthyl group, as well as a phenyl group.

Each of the heterocyclic group which may be substituted represented by each of $R^1$, $R^2$, $R^5$ and Q, the heterocyclic group represented by Cy and the heterocyclic moiety in each of the secondary substituent and the tertiary substituent as described hereinafter, may, for example, be a five-membered monocyclic heterocyclic group such as a pyrrolyl group, a pyrrolinyl group, a pyrrolidinyl group, a furanyl group, a dihydrofuranyl group, a tetrahydrofuranyl group, a thienyl group, a dihydrothienyl group, a tetrahydrothienyl group, a pyrazolyl group, a pyrazolinyl group, a pyrazolidinyl group, an imidazolyl group, an imidazolinyl group, an imidazolidinyl group, an oxazolyl group, an oxazolinyl group, an oxazolidinyl group, an isoxazolyl group, an isoxazolinyl group, an isoxazolidinyl group, a thiazolyl group, a thiazolinyl group, a thiazolidinyl group, an isothiazolyl group, an isothiazolinyl group, an isothiazolidinyl group, an oxadiazolyl group, an oxadiazolinyl group, an oxadiazolidinyl group, a thiadiazolyl group, a thiadiazolinyl group, a thiadiazolidinyl group, a triazolyl group, a triazolinyl group, a triazolidinyl group, a tetrazolyl group, a tetrazolinyl group, a tetrazolidinyl group, a dioxolyl group, a dioxolanyl group, a dithiolyl group or a dithiolanyl group; a six-membered monocyclic heterocyclic group such as a pyridyl group, a dihydropyridyl group, a tetrahydropyridyl group, a piperidinyl group, a pyrimidyl group, a dihydropyrimidyl group, a tetrahydropyrimidyl group, a hexahydropyrimidyl group, a pyridazinyl group, a dihydropyridazinyl group, a tetrahydropyridazinyl group, a hexahydropyridazinyl group, a pyrazinyl group, a dihydropyrazinyl group, a tertahydropyrazinyl group, a piperazinyl group, a triazinyl group, a dihydrotriazinyl group, a tetrahydrotriazinyl group, a hexahydrotriazinyl group, a pyranyl group, a dihydropyranyl group, a tetrahydropyranyl group, a dioxinyl group, a dioxenyl group, a dioxanyl group, a dithianyl group or a morpholinyl group; a fused-polycyclic heterocyclic group such as a thienothienyl group, a dihydrocyclopentathienyl group, an indolyl group, a tetrahydroindolyl group, an isoindolyl group, a tetrahydroisoindolyl group, a benzothienyl group, a tetrahydrobenzothienyl group, a benzofuranyl group, a tetrahydrobenzofuranyl group, a benzoxazolyl group, a tetrahydrobenzoxazolyl group, a benzisoxazolyl group, a tetrahydrobenzisoxazolyl group, a benzothiazolyl group, a tetrahydrobenzothiazolyl group, a benzisothiazolyl group, a tetrahydrobenzisothiazolyl group, a benzimidazolyl group, a tetrahydrobenzimidazolyl group, a benzodioxolyl group, a benzodithiolyl group, a benzodioxanyl group, a benzodithianyl group, a quinolinyl group, an isoquinolinyl group, a quinazolinyl group, a quinoxalinyl group, a phthalazinyl group, a naphthylidinyl group or a purinyl group; or a crosslinked polycyclic heterocyclic group such as a quinuclidinyl group.

The secondary substituent of each of the alkyl group which may be substituted, the alkenyl group which may be substituted and the alkynyl group which may be substituted, may, for example, be a halogen atom, a hydroxyl group, a mercapto group, an alkoxy group, a substitutable alkylthio group, a substitutable alkenyloxy group, a substitutable alkenylthio group, a substitutable alkynyloxy group, a substitutable alkynylthio group, a substitutable cycloalkyl group, a substitutable cycloalkenyl group, a substitutable cycloalkoxy group, a substitutable cycloalkylthio group, a substitutable cycloalkenyloxy group, a substitutable cycloalkenylthio group, a substitutable alkoxycarbonyl group, a substitutable alkylcarbonyl group, a substitutable alkylcarbonyloxy group, a substitutable alkenyloxycarbonyl group, a substitutable alkenylcarbonyl group, a substitutable alkenylcarbonyloxy group, a substitutable alkynyloxycarbonyl group, a substitutable alkynylcarbonyl group, a substitutable alkynylcarbonyloxy group, a substitutable cycloalkoxycarbonyl group, a substitutable cycloalkylcarbonyl group, a substitutable cycloalkylcarbonyloxy group, a substitutable cycloalkenyloxycarbonyl group, a substitutable cycloalkenylcarbonyl group, a substitutable cycloalkenylcarbonyloxy group, a substitutable aryl group, a substitutable aryloxy group, a substitutable arylthio group, a substitutable aryloxycarbonyl group, a substitutable arylcarbonyl group, a substitutable arylcarbonyloxy group, a substitutable heterocyclic group, a substitutable heterocyclyloxy group, a substitutable heterocyclylthio group, a substitutable heterocyclyloxycarbonyl group, a substitutable heterocyclylcarbonyl group, a substitutable heterocyclylcarbonyloxy group, a substitutable amino group, a cyano group, a nitro group, a carboxyl group, a substitutable aminocarbonyl group, a substitutable alkylsulfonyl group, a substitutable alkenylsulfonyl group, a substitutable alkynylsulfonyl group, a substitutable cycloalkylsulfonyl group, a substitutable cycloalkenylsulfonyl group, a substitutable arylsulfonyl group, a substitutable heterocyclylsulfonyl group or a substitutable aminosulfonyl group. The number of such substituents may be one or two or more, and such substituents may be the same or different.

The secondary substituent of each of the cycloalkyl group which may be substituted, the cycloalkenyl group which may be substituted, the aryl group which may be substituted and the heterocyclic group which may be substituted, may, for example, be a halogen atom, a hydroxyl group, a mercapto group, a substitutable alkyl group, a substitutable alkenyl group, a substitutable alkynyl group, a substitutable alkoxy group, a substitutable alkylthio group, a substitutable alkenyloxy group, a substitutable alkenylthio group, a substitutable alkynyloxy group, a substitutable alkynylthio group, a substitutable cycloalkyl group, a substitutable cycloalkenyl group, a substitutable cycloalkoxy group, a substitutable cycloalkylthio group, a substitutable cycloalkenyloxy group, a substitutable cycloalkenylthio group, a substitutable alkoxycarbonyl group, a substitutable alkylcarbonyl group, a substitutable alkylcarbonyloxy group, a substitutable alkenyloxycarbonyl group, a substitutable alkenylcarbonyl group, a substitutable alkenylcarbonyloxy group, a substitutable alkynyloxycarbonyl group, a substitutable alkynylcarbonyl group, a substitutable alkynylcarbonyloxy group, a substitutable cycloalkoxycarbonyl group, a substitutable cycloalkylcarbonyl group, a substitutable cycloalkylcarbonyloxy group, a substitutable cycloalkenyloxycarbonyl group, a substitutable cycloalkenylcarbonyl group, a substitutable cycloalkenylcarbonyloxy group, a substitutable aryl group, a substitutable aryloxy group, a substitutable arylthio group, a substitutable aryloxycarbonyl group, a substitutable arylcarbonyl group, a substitutable arylcarbonyloxy group, a substitutable heterocyclic group, a substitutable heterocyclyloxy group, a substitutable heterocyclylthio group, a substitutable heterocyclyloxycarbonyl group, a substitutable heterocyclylcarbonyl group, a substitutable heterocyclylcarbonyloxy group, a substitutable amino group, a cyano group, a nitro group, a carboxyl group, a substitutable aminocarbonyl group, a substitutable alkylsulfonyl group, a substitutable alkenylsulfonyl group, a substitutable alkynylsulfonyl group, a substitutable cycloalkylsulfonyl group, a substitutable cycloalkenylsulfonyl group, a substitutable arylsulfonyl group, a substitutable heterocyclylsulfonyl group or a substitutable aminosulfonyl group. The number of such substituents may be one or two or more, and such substituents may be the same or different.

The secondary substituent of the amino group which may be substituted represented by each of $R^1$, $R^2$ and Q, may, for example, be a hydroxyl group, a substitutable alkyl group, a substitutable alkenyl group, a substitutable alkynyl group, a substitutable alkoxy group, a substitutable alkenyloxy group, a substitutable alkynyloxy group, a substitutable cycloalkyl group, a substitutable cycloalkenyl group, a substitutable cycloalkoxy group, a substitutable cycloalkenyloxy group, a substitutable alkoxycarbonyl group, a substitutable alkylcarbonyl group, a substitutable alkenyloxycarbonyl group, a substitutable alkenylcarbonyl group, a substitutable alkynyloxycarbonyl group, a substitutable alkynylcarbonyl group, a substitutable cycloalkoxycarbonyl group, a substitutable cycloalkylcarbonyl group, a substitutable cycloalkenyloxycarbonyl group, a substitutable cycloalkenylcarbonyl group, a substitutable aryl group, a substitutable aryloxy group, a substitutable aryloxycarbonyl group, a substitutable arylcarbonyl group, a substitutable heterocyclic group, a substitutable heterocyclyloxy group, a substitutable heterocyclyloxycarbonyl group, a substitutable heterocyclylcarbonyl group, a substitutable aminocarbonyl group, a substitutable alkylsulfonyl group, a substitutable alkenylsulfonyl group, a substitutable alkynylsulfonyl group, a substitutable cycloalkylsulfonyl group, a substitutable cycloalkenylsulfonyl group, a substitutable arylsulfonyl group, a substitutable heterocyclylsulfonyl group or a substitutable aminosulfonyl group. The number of such secondary substituents may be one or two or more, and such secondary substituents may be the same or different. Further, the two secondary substituents may form a ring containing or not containing a heteroatom.

The tertiary substituent of each of substitutable groups among the above secondary substituents may, for example, be a halogen atom, a hydroxyl group, a mercapto group, a cyano group, a nitro group, a carboxyl group, an amino group, an alkyl group, an alkenyl group, an alkynyl group, a cycloalkyl group, a cycloalkenyl group, an aryl group, a heterocyclic group, an alkoxy group, an alkenyloxy group, an alkynyloxy group, a cycloalkyloxy group, a cycloalkenyloxy group, an aryloxy group, a heterocyclyloxy group, an alkylthio group, an alkenylthio group, an alkynylthio group, a cycloalkylthio group, a cycloalkenylthio group, an arylthio group, a heterocyclylthio group, an alkylsulfonyl group, an alkenylsulfonyl group, an alkynylsulfonyl group, a cycloalkylsulfonyl group, a cycloalkenylsulfonyl group, an arylsulfonyl group, a heterocyclylsulfonyl group, an alkylcarbonyl group, an alkenylcarbonyl group, an alkynylcarbonyl group, a cycloalkylcarbonyl group, a cycloalkenylcarbonyl group, an arylcarbonyl group, a heterocyclylcarbonyl group, an alkyloxycarbonyl group, an alkenyloxycarbonyl group, an alkynyloxycarbonyl group, a cycloalkyloxycarbonyl group, a cycloalkenyloxycarbonyl group, an aryloxycarbonyl group, a heterocyclyloxycarbonyl group, an aminocarbonyl group, an alkylaminocarbonyl group, a dialkylaminocarbonyl group, an alkenylaminocarbonyl group, an alkynylaminocarbonyl group, a cycloalkylaminocarbonyl group, a cycloalkenylaminocarbonyl group, an arylaminocarbonyl group, a heterocyclylaminocarbonyl group, an aminosulfonyl group, an alkylaminosulfonyl group, a dialkylaminosulfonyl group, an alkenylaminosulfonyl group, an alkynylaminosulfonyl group, a cycloalkylaminosulfonyl group, a cycloalkenylaminosulfonyl group, an arylaminosulfonyl group, a heterocyclylaminosulfonyl group, an alkylamino group, a dialkylamino group, an alkenylamino group, an alkynylamino group, a cycloalkylamino group, a cycloalkenylamino group, an arylamino group, a heterocyclylamino group, an alkylcarbonylamino group, an alkenylcarbonylamino group, an alkynylcarbonylamino group, a cycloalkylcarbonylamino group, a cycloalkenylcarbonylamino group, an arylcarbonylamino group, a heterocyclylcarbonylamino group, an alkylsulfonylamino group, an alkenylsulfonylamino group, an alkynylsulfonylamino group, a cycloalkylsulfonylamino group, a cycloalkenylsulfonylamino group, an arylsulfonylamino group or a heterocyclylsulfonylamino group. The number of such tertiary substituents may be one or two or more, and when the number is two or more, such substituents may be the same or different. Further, when the secondary substituent is an amino group substituted with two tertiary substituents, such tertiary substituents together may form a ring containing or not containing a heteroatom.

Further, each of the alkyl moiety, the alkenyl moiety, the alkynyl moiety, the cycloalkyl moiety, the cycloalkenyl moiety, the aryl moiety and the heterocyclic moiety of each of such tertiary substituents may further be substituted with a quaternary substituent such as a halogen atom, a hydroxyl group, a mercapto group, a cyano group, a nitro group, a carboxyl group, an amino group, an alkyl group, a haloalkyl group, an alkoxy group, a haloalkoxy group, an alkylthio group, a haloalkylthio group, an alkoxycarbonyl group, an aminocarbonyl group, an alkylaminocarbonyl group, a dialkylaminocarbonyl group, an aminosulfonyl group, an alkylaminosulfonyl group, a dialkylaminosulfonyl group, an alkylamino group, a dialkylamino group, an alkylcarbonylamino group, an alkylsulfonylamino group, a cycloalkyl group, an aryl group or a heterocyclic group. The number of such substituents may be one or two or more, and when the number of the substituents is two or more, such substituents may be the same or different.

BEST MODE FOR CARRYING OUT THE INVENTION

Now, some of preferred embodiments of the present invention will be explained, however, the present invention is by no means restricted thereto.

The compounds of the above formula (I) are compounds useful as an active ingredient of cytokine production inhibitors, and are useful as preventive or therapeutic medicines for diseases accompanied by hyperactivated immune functions as listed below.

(1) At least one type of allergic diseases selected from urticaria, food allergy, anaphylactic shock, hypereosinophilic syndrome, asthma, allergic rhinitis, allergic conjunctivitis and atopic dermatitis.

(2) Systemic autoimmune diseases in which antibody production or humoral immunity is hyperactivated.

(3) At least one type of organ specific autoimmune diseases selected from chronic rheumatoid arthritis, type I diabetes, Hashimoto's thyroiditis, myasthenia gravis and multiple sclerosis.

(4) Graft rejection accompanying organ transplantation.

Among the compounds of the above formula (I) and salts thereof, compounds wherein Cy is a phenyl group or a six-membered monocyclic heterocyclic group or salts thereof are preferred as an active ingredient of the cytokine production inhibitors, and among them, more preferred compounds are listed below.

(1) Aniline derivatives of the formula (I') or salts thereof:

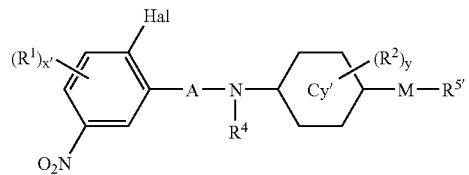

[wherein A, $R^1$, $R^2$, $R^4$ and y are as defined above; Hal is a halogen atom; Cy' is a phenyl group or a 6-membered monocyclic heterocyclic group; M is O, S, a $NR^6$ group (wherein $R^6$ is as defined above)., $-OCH_2-$, $-OCH_2CH_2-$, $-CH_2O-$, $-CH_2CH_2O-$, $-SCH_2-$, $-SCH_2CH_2-$, $-CH_2S-$, $-CH_2CH_2S-$ or a single bond; $R^5$ is a pyridyl group which may be substituted or an adamantyl group which may be substituted; and x' is an integer of from 0 to 3; provided that a case where A is CO, and $R^{5'}$ is an adamantyl group substituted with a $-(CR^aR^a)$ d-$NCR^bR^c$ group (wherein $R^a$ is a hydrogen atom or an alkyl group; $R^b$ is a hydrogen atom, an alkyl group or an acyl group, $R^c$ is a hydrogen atom or an alkyl group, and d is an integer of from 0 to 3) is excluded].

(2) The aniline derivatives of the formula (I') or salts thereof, wherein A is CO.

(3) The aniline derivatives of the formula (I') or salts thereof, wherein A is CO, and $R^{5'}$ is a pyridyl group which may be substituted.

(4) The aniline derivatives of the formula (I') or salts thereof, wherein A is CO, and $R^{5'}$ is a pyridyl group substituted with a haloalkyl group (provided that the pyridyl group may be substituted with at least one substituent selected from the group consisting of a halogen atom, a hydroxyl group, a mercapto group, a substitutable alkyl group, a substitutable alkenyl group, a substitutable alkynyl group, a substitutable alkoxy group, a substitutable alkylthio group, a substitutable alkenyloxy group, a substitutable alkenylthio group, a substitutable alkynyloxy group, a substitutable alkynylthio group, a substitutable cycloalkyl group, a substitutable cycloalkenyl group, a substitutable cycloalkoxy group, a substitutable cycloalkylthio group, a substitutable cycloalkenyloxy group, a substitutable cycloalkenylthio group, a substitutable alkoxycarbonyl group, a substitutable alkylcarbonyl group, a substitutable alkylcarbonyloxy group, a substitutable alkenyloxycarbonyl group, a substitutable alkenylcarbonyl group, a substitutable alkenylcarbonyloxy group, a substitutable alkynyloxycarbonyl group, a substitutable alkynylcarbonyl group, a substitutable alkynylcarbonyloxy group, a substitutable cycloalkoxycarbonyl group, a substitutable cycloalkylcarbonyl group, a substitutable cycloalkylcarbonyloxy group, a substitutable cycloalkenyloxycarbonyl group, a substitutable cycloalkenylcarbonyl group, a substitutable cycloalkenylcarbonyloxy group, a substitutable aryl group, a substitutable aryloxy group, a substitutable arylthio group, a substitutable aryloxycarbonyl group, a substitutable arylcarbonyl group, a substitutable arylcarbonyloxy group, a substitutable heterocyclic group, a substitutable heterocyclyloxy group, a substitutable heterocyclylthio group, a substitutable heterocyclyloxycarbonyl group, a substitutable heterocyclylcarbonyl group, a substitutable heterocyclylcarbonyloxy group, a substitutable amino group, a cyano group, a nitro group, a carboxyl group, a substitutable aminocarbonyl group, a substitutable alkylsulfonyl group, a substitutable alkenylsulfonyl group, a substitutable alkynylsulfonyl group, a substitutable cycloalkylsulfonyl group, a substitutable cycloalkenylsulfonyl group, a substitutable arylsulfonyl group, a substitutable heterocyclylsulfonyl group and a substitutable aminosulfonyl group).

(5) The aniline derivatives of the formula (I') or salts thereof, wherein A is CO, $R^{5'}$ is a pyridyl group substituted with a haloalkyl group, and the pyridyl group may further be substituted with at least one halogen atom.

(6) The aniline derivatives of the formula (I') or salts thereof, wherein A is CO, and $R^{5'}$ is a 3-chloro-5-trifluoromethyl-2-pyridyl group.

(7) The aniline derivatives of the formula (I') or salts thereof, wherein A is CO, and $R^{5'}$ is an adamantyl group which may be substituted.

(8) The aniline derivatives of the formula (I') or salts thereof, wherein A is CO; Hal is a chlorine atom; and $R^{5'}$ is an adamantyl group which may be substituted.

(9) The aniline derivatives of the formula (I') or salts thereof, wherein A is CO; Hal is a fluorine atom, a bromine atom or an iodine atom; and $R^{5'}$ is an adamantyl group which may be substituted.

(10) The aniline derivatives of the formula (I') or salts thereof, wherein A is $SO_2$.

(11) The aniline derivatives of the formula (I') or salts thereof, wherein the 6-membered monocyclic heterocyclic group represented by Cy' is a 6-membered heteroaryl group.

(12) The aniline derivatives or salts thereof as defined in (11), wherein the 6-membered heteroaryl group is a pyridyl group, a pyrimidinyl group, a pyridazinyl group or a pyrazinyl group.

(13) The aniline derivatives of the formula (I'') or salts thereof:

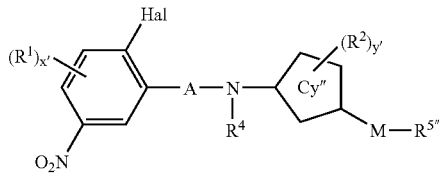

[wherein A, $R^1$, $R^2$, $R^4$, Hal, M and x' are as defined above; Cy'' is a 5-membered monocyclic heterocyclic group; $R^{5''}$ is a phenyl group which may be substituted, a pyridyl group which may be substituted or an adamantyl group which may be substituted; and y' is an integer of from 0 to 3].

(14) The aniline derivatives of the formula (I'') or salts thereof, wherein A is CO.

(15) The aniline derivatives of the formula (I'') or salts thereof, wherein A is CO, and $R^{5''}$ is a phenyl group which may be substituted or a pyridyl group which may be substituted.

(16) The aniline derivatives of the formula (I'') or salts thereof, wherein A is CO, and $R^{5''}$ is an adamantyl group which may be substituted.

(17) The aniline derivatives of the formula (I'') or salts thereof, wherein A is CO, M is an oxygen atom, a sulfur atom or a $NR^6$ group (wherein $R^6$ is as defined in claim 1); and $R^{5''}$ is a pyridyl group which may be substituted or an adamantyl group which may be substituted.

(18) The aniline derivatives of the formula (I'') or salts thereof, wherein A is $SO_2$.

(19) The aniline derivatives of the formula (I'') or salts thereof, wherein the 5-membered monocyclic heterocyclic group represented by Cy'' is a 5-membered heteroaryl group.

(20) The aniline derivatives or salts thereof as defined in (19) wherein the 5-membered heteroaryl group is a furanyl group, a thienyl group, an imidazolyl group, an oxazolyl group, a pyrroyl group, an oxadiazolyl group, a thiadiazolyl group or a thiazolyl group.

The compounds of the above formula (I) and salts thereof can be produced by a process for producing known analogous compounds, or a method in accordance therewith, and as preferred embodiments, the following Preparation Methods [1] and [2] will be exemplified.

[1] Preparation Method 1

A method for producing the aniline derivative of the above formula (I) or a salt thereof, by reacting a compound of the formula (IV):

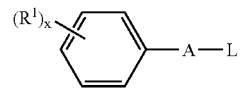

[wherein A, $R^1$ and x are as defined above, and L is a leaving group] with a compound of the formula (V):

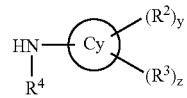

[wherein Cy, $R^2$, $R^3$, $R^4$, y and z are as defined above]. As the leaving group represented by L may, for example, be a halogen atom.

The reaction of the Preparation Method 1 may be carried out in the presence of a proper solvent. The specific solvent used may, for example, be an aromatic hydrocarbon such as benzene, toluene or xylene; an aliphatic hydrocarbon such as pentane, hexane, heptane, petroleum ether, ligroin or petroleum benzine; an ether such as diethyl ether, dipropyl ether, dibutyl ether, tetrahydrofuran or dioxane; a nitrile such as acetonitrile or propionitrile; an acid amide such as dimethylformamide or dimethylacetamide; a sulfoxide such as dimethylsulfoxide; a sulfone such as sulfolane; a phosphate amide such as hexamethylphosphoramide; or a halogenated hydrocarbon such as chloroform, dichloromethane, carbon tetrachloride or 1,2-dichloroethane, or a mixed solvent thereof.

In the Preparation Method 1, the reaction is carried out preferably in the presence of a base in some cases. The specific base used may, for example, be an organic base such as triethylamine, pyridine, N-methylmorpholine, 1,8-diazabicyclo[5,4,0]-7-undecene or N,N-dimethylaniline; an alkali metal such as lithium, sodium or potassium; a carbonate of an alkali metal such as lithium carbonate, sodium carbonate or potassium carbonate; a hydrogencarbonate of an alkali metal such as lithium hydrogencarbonate, sodium hydrogencarbonate or potassium hydrogencarbonate; a hydride of an alkali metal such as lithium hydride, sodium hydride or potassium hydride; or n-butyllithium, lithium diisopropylamide or sodium amide.

The reaction of the Preparation Method 1 is carried out usually at a reaction temperature of from −70 to 150° C., preferably at a reaction temperature of from −10 to 100° C. The reaction time is usually from 0.1 to 48 hours.

In the Preparation Method 1, the compound of the formula (III) may be used in an amount of from 0.8 to 2 equivalents, preferably from 1 to 1.5 equivalents, per 1 mol of the compound of the above formula (II).

In the Preparation Method 1, various reaction conditions may optionally be combined with one another. Further, such various reaction conditions include reaction conditions in a usual range and reaction conditions in a preferred range, and they may also be optionally selected and combined with one another.

[2] Preparation Method 2

A method for producing an aniline derivative of the formula (I-2):

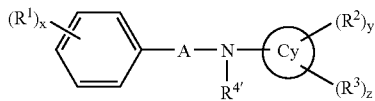

[wherein A, Cy, $R^1$, $R^2$, $R^3$, $R^{4'}$, x, y and z are as defined above], by reacting a compound of the formula (I-1):

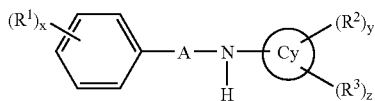

[wherein A, Cy, $R^1$, $R^2$, $R^3$, x, y and z are as defined above] with a compound of the formula (VI): $R^{4'}$-L [wherein $R^{4'}$ is an alkyl group which may be substituted, and L is as defined above].

The reaction of the Preparation Method 2 may be carried out in the presence of a proper solvent. The specific solvent used may, for example, be an aromatic hydrocarbon such as benzene, toluene or xylene; an aliphatic hydrocarbon such as pentane, hexane, heptane, petroleum ether, ligroin or petroleum benzine; an ether such as diethyl ether, dipropyl ether, dibutyl ether, tetrahydrofuran or dioxane; a nitrile such as acetonitrile or propionitrile; an acid amide such as dimethylformamide or dimethylacetamide; a sulfoxide such as dimethylsulfoxide; a sulfone such as sulfolane; a phosphate amide such as hexamethylphosphoramide; or a halogenated hydrocarbon such as chloroform, dichloromethane, carbon tetrachloride or 1,2-dichloroethane, or a mixed solvent thereof.

In the Preparation Method 2, the reaction is carried out preferably in the presence of a base, so as to carry out the reaction efficiently. The specific base used may, for example, be an organic base such as triethylamine, pyridine, N-methylmorpholine, 1,8-diazabicyclo[5,4,0]-7-undecene or N,N-dimethylaniline; an alkali metal such as lithium, sodium or potassium; a carbonate of an alkali metal such as lithium carbonate, sodium carbonate or potassium carbonate; a hydrogencarbonate of an alkali metal such as lithium hydrogencarbonate, sodium hydrogencarbonate or potassium hydrogencarbonate; a hydride of an alkali metal such as lithium hydride, sodium hydride or potassium hydride; or n-butyllithium, lithium diisopropylamide or sodium amide.

The reaction of the Preparation Method 2 is carried out usually at a reaction temperature of from −70 to 150° C., preferably at a reaction temperature of from −10 to 100° C. The reaction time is usually from 0.1 to 48 hours.

In the Preparation Method 2, the compound of the formula (IV) may be used in an amount of from 0.8 to 2 equivalents, preferably from 1 to 1.5 equivalents, per 1 mol of the compound of the above formula (I-1).

In the Preparation Method 2, various reaction conditions may optionally be combined with one another. Further, such various reaction conditions include reaction conditions in a usual range and reaction conditions in a preferred range, and they may also be optionally selected and combined with one another.

The compounds of the above formula (I) obtained by each of the above Preparation Methods 1 and 2 and methods in accordance therewith, may be isolated and purified by means of a known method such as concentration, concentration under reduced pressure, distillation, fractionation, redistribution, solvent extraction, crystallization, recrystallization or chromatography.

In a case where the compound of the above formula (I) is obtained as a free form, a salt may be formed by a conventional method. Further, the compound of the above formula (I) or a salt thereof or a stereoisomer thereof has a cytokine production inhibitory effect by itself or as mixed.

Among the compounds of the above formula (I) and salts thereof, the compounds of the formula (I') and salts thereof may be produced by the following Preparation Method [A] or [B] or a combination of these Preparation Methods, in accordance with the above Preparation Method 1 and 2.

[A] A method for producing the aniline derivative of the above formula (I') or a salt thereof, by reacting a compound of the formula (II):

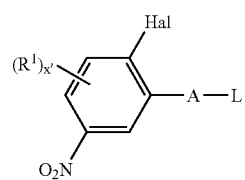

[wherein A, $R^1$, Hal and x' are as defined above, and L is a leaving group] with a compound of the formula (III):

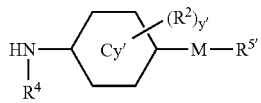

[wherein Cy', $R^2$, $R^4$, $R^{5'}$, M and y' are as defined above] The Preparation Method [A] is in accordance with the Preparation Method 1, and reaction conditions in the Preparation Method 1 can be applied.

[B] A method for producing an aniline derivative of the formula (I'-2) or a salt thereof:

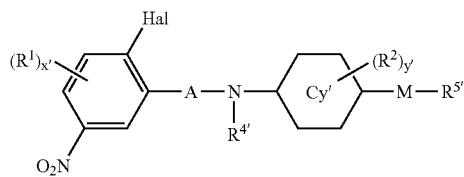

[wherein A, Cy', Hal, $R^1$, $R^2$, $R^{4'}$, $R^{5'}$, M, x' and y' are as defined above], by reacting a compound of the formula (I'-1):

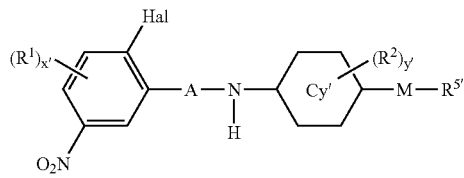

[wherein A, Cy', Hal, $R^1$, $R^2$, $R^{5'}$, M, x' and y' are as defined above] with a compound of the formula (VI): $R^{4'}$-L [wherein $R^{4'}$ is an alkyl group which may be substituted, and L is as defined above].

The Preparation Method [B] is in accordance with the Preparation Method 2, and reaction conditions in the Preparation Method 2 can be applied.

The compounds of the formula [I] of the present invention are usually used in the form of a common pharmaceutical preparation (such as a method as defined in the Japanese Pharmacopoeia Twelfth Edition). The pharmaceutical preparation is prepared by using a commonly used diluent or excipient such as a bulking agent, an extender, a binding agent, a moisture-imparting agent, a disintegrator, a surfactant or a lubricant. As the pharmaceutical preparation, various forms may be selected depending upon the purpose of treatment, and a tablet, a pill, a powder, a dust, a granule, a capsule, a suppository, a solution, a suspension, an emulsion, an injection (such as a solution or a suspension), a spray, an aerosol, a cream, an ointment, a lotion or a transdermal agent (a patch, a matrix or a tape) may be mentioned as examples.

To form the medicine into a tablet, carriers which have conventionally been known in this field can be used widely, and they may, for example, be excipients such as lactose, sucrose, sodium chloride, glucose, urea, starch, calcium carbonate, kaolin, crystalline cellulose and silicic acid, binding agents such as water, ethanol, propanol, simple syrup, a glucose solution, a starch solution, a gelatin solution, carboxymethyl cellulose, Shellac, methyl cellulose, potassium phosphate and polyvinyl pyrrolidone, disintegrators such as dried starch, sodium alginate, an agar-powder, a laminaran powder, sodium hydrogencarbonate, calcium carbonate, polyoxyethylene sorbitan fatty acid esters, sodium lauryl sulfate, monoglyceryl stearate, starch and lactose, disintegration inhibitors such as sucrose, stearin, cacao butter and hydrogenated oil, absorption stimulators such as a quaternary ammonium base and sodium lauryl sulfate, moisturizers such as glycerin and starch, absorbents such as starch, lactose, kaolin, bentonite and colloidal silicate, and lubricants such as purified talc, a stearate, a boric acid powder and polyethylene glycol. Further, a tablet may be a tablet having a common coating applied thereto as the case requires, such as a sugar-coated tablet, a gelatin-coated tablet, an enteric-coated tablet or a film-coated tablet, or a double tablet or a multilayer tablet.

To form the medicine into a pill, carriers which have conventionally been known in this field can be used widely, and they may, for example, be excipients such as glucose, lactose, starch, cacao butter, hydrogenated vegetable oil, kaolin and talc, binding agents such as powdered acacia, powdered tragacanth, gelatin and ethanol and disintegrators such as laminaran agar.

To form the medicine into a suppository, conventionally known carriers can be used widely, and they may, for example, be polyethylene glycol, cacao butter, higher alcohols, higher alcohol esters, gelatin and semi-synthetic glyceride.

To prepare an injection, a solution, an emulsion or a suspension is sterilized, and is preferably isotonic with the blood, and to form the medicine into a solution, an emulsion or a suspension, all the diluents which are commonly used in this field can be used, and they may, for example, be water, a lactic acid aqueous solution, ethyl alcohol, propylene glycol, ethoxylated isostearyl alcohol, polyoxylated isostearyl alcohol and polyoxyethylene sorbitan fatty acid esters. In this case, sodium chloride salt, glucose or glycerin in an amount adequate to prepare an isotonic solution may be incorporated in the pharmaceutical preparation, and a common solubilizing agent, buffer, soothing agent or the like may be added thereto. Further, as the case requires, a colorant, a preservative, a fragrant material, a flavoring agent, a sweetener or another pharmaceutical agent may be incorporated in the pharmaceutical preparation.

The amount of the compound of the formula (I) of the present invention is not particularly limited and may optionally be selected from a wide range, but it is usually from 1 to 70 wt %, preferably from 5 to 50 wt % in the entire composition.

The administration method of the compounds of the formula (I) of the present invention is not particularly limited, and they are orally or parenterally administered by a method depending upon the form of the preparation, the age, the sex or other conditions of the patient and the degree of the disease. For example, for oral administration, a tablet, a pill, a solution, a suspension, an emulsion, a granule or a capsule may, for example, be mentioned as a preferred form. For parenteral administration, the medicine may be administered in the form of e.g. a topical agent, an injection, a transdermal agent, nasal drops, an inhalant or a suppository. In the case of an injection, it is preferred that the medicine is intravenously administered by itself or as mixed with a conventional fluid replacement such as glucose or amino acids, or as the case requires, it is intramuscularly, intradermally, subcutaneously or intraperitoneally administered by itself. Further, in the case of a suppository, it is preferred that the medicine is administered in rectum.

The dose of the compound of the formula (I) of the present invention is optionally selected depending upon e.g. the dose regimen, the age, the sex or other conditions of the patient and the degree of disease, and usually the amount of the compound of the above formula (I) as an active ingredient is preferably from about 0.05 to about 50 mg per kg of the body weight per day, and the medicine may be administered once or several times a day. Further, it is preferred that the active ingredient is contained in an amount of from 1 to 1,000 mg in the administration unit form.

EXAMPLES

Now, Examples (Preparation Examples and Test Examples) of the present invention will be described, however, the present invention is by no means restricted thereto.

Preparation Example 1

Preparation of N-(4-phenoxyphenyl)-2-chloro-5-nitrobenzamide (Compound No. 27)

Into 5 mL of a tetrahydrofuran solution comprising 420 mg of 4-phenoxyaniline and 250 mg of triethylamine, 5 mL of a tetrahydrofuran solution comprising 500 mg of 2-chloro-5-nitrobenzoylchloride was dropwise added under cooling with ice. After stirring for about 30 minutes, water was added thereto, and precipitated crystals were collected by filtration. The collected crystals were washed with water and then dried to obtain 730 mg of N-(4-phenoxyphenyl)-2-chloro-5-nitrobenzamide (Compound No. 27) having a melting point of 128° C.

Preparation Example 2

Preparation of N-(4-(1-adamantyl)-2-methylphenyl)-2-bromo-5-nitrobenzamide (Compound No. 46)

To 5 mL of a tetrahydrofuran solution comprising 300 mg of 4-(1-adamantyl)-2-methylaniline hydrochloride and 120 mg of triethylamine, 5 mL of a tetrahydrofuran solution comprising 290 mg of 2-bromo-5-nitrobenzoylchloride was dropwise added under cooling with ice. After stirring for about 30 minutes, water was added thereto, and the precipitated crystals were collected by filtration. The collected crystals were washed with water and then dried to obtain 310 mg of N-(4-(1-adamantyl)-2-methylphenyl)-2-bromo-5-nitrobenzamide (Compound No. 46) having a melting point of 229° C.

Preparation Example 3

Preparation of N-(4-(1-adamantyl)-2-methylphenyl)-2-chloro-5-nitrobenzenesulfonamide (Compound No. 48)

To 5 mL of a tetrahydrofuran solution comprising 250 mg of 4-(1-adamantyl)-2-methylaniline hydrochloride and 200 mg of triethylamine, 5 mL of a tetrahydrofuran solution comprising 230 mg of 2-chloro-5-nitrobenzenesulfonylchloride was dropwise added, followed by stirring at about 40° C. for about 7 hours. After the mixture was left to stand for cooling, water was added thereto, extraction with chloroform, drying over salt cake and concentration under reduced pressure were carried out to obtain crude crystals. The crude crystals were recrystalized from ether to obtain 150 mg of N-(4-(1-adamantyl)-2-methylphenyl)-2-chloro-5-nitrobenzenesulfonamide (Compound No. 48) having a melting point of 238° C.

Preparation Example 4

Preparation of N-(4-(3-chloro-5-trifluoromethyl-2-pyridyloxy)-3-methylphenyl)-2-chloro-5-nitrobenzamide (Compound No. 106)

To 5 mL of a tetrahydrofuran solution comprising 670 mg of 4-(3-chloro-5-trifluoromethyl-2-pyridyloxy)-3-methylaniline and 270 mg of triethylamine, 5 mL of a tetrahydrofuran solution comprising 490 mg of 2-chloro-5-nitrobenzoylchloride was dropwise added, followed by stirring for about 30 minutes, and then water was added, and the precipitated crystals were collected by filtration. The collected crystals were washed with water and then dried to obtain 700 mg of N-(4-(3-chloro-5-trifluoromethyl-2-pyridyloxy)-3-methylphenyl)-2-chloro-5-nitrobenzamide (Compound No. 106) having a melting point of from 230 to 232° C.

Preparation Example 5

Preparation of N-(2-(1-adamantyloxy)-5-pyridyl)-2-chloro-5-nitrobenzamide (Compound No. 123)

To 5 mL of a tetrahydrofuran solution comprising 290 mg of 5-amino-2-(1-adamantyloxy)pyridine) and 150 mg of triethylamine, 5 mL of a tetrahydrofuran solution comprising 260 mg of 2-chloro-5-nitrobenzoylchloride was dropwise added, followed by stirring for about 30 minutes, and then water was added, and the precipitated crystals were collected by filtration. The collected crystals were washed with water and then dried to obtain 330 mg of N-(2-(1-adamantyloxy)-5-pyridyl)-2-chloro-5-nitrobenzamide (Compound No. 123) having a melting point of from 98 to 105° C.

Preparation Example 6

Preparation of N-(4-(3-chloro-5-trifluoromethyl-2-pyridyloxy)-3-(1-pyrrolyl)phenyl)-2-chloro-5-nitrobenzamide (Compound No. 127)

To 5 mL of a tetrahydrofuran solution comprising 320 mg of 4-(3-chloro-5-trifluoromethyl-2-pyridyloxy)-3-(1-pyrrolyl)aniline and 110 mg of triethylamine, 5 mL of a tetrahydrofuran solution comprising 200 mg of 2-chloro-5-nitrobenzoylchloride was dropwise added, followed by stirring for about 30 minutes, and then water was added, and the precipitated crystals were collected by filtration. The collected crystals were washed with water and then dried to obtain 260 mg of N-(4-(3-chloro-5-trifluoromethyl-2-pyridyloxy)-3-(1-pyrrolyl)phenyl)-2-chloro-5-nitrobenzamide (Compound No. 127) having a melting point of from 165 to 167° C.

Preparation Example 7

Preparation of N-(4-(3-chloro-5-trifluoromethyl-2-pyridylmethyloxy)phenyl)-2-chloro-5-nitrobenzamide (Compound No. 135)

To 5 mL of a tetrahydrofuran solution comprising 300 mg of 4-(3-chloro-5-trifluoromethyl-2-pyridylmethyloxy)aniline and 120 mg of triethylamine, 5 mL of a tetrahydrofuran solution comprising 220 mg of 2-chloro-5-nitrobenzoylchloride was dropwise added, followed by stirring for about 30 minutes, and then water was added thereto, and the precipitated crystals were collected by filtration. The collected crystals were washed with water and then dried to obtain 380 mg of N-(4-(3-chloro-5-trifluoromethyl-2-pyridylmethyloxy)phenyl)-2-chloro-5-nitrobenzamide (Compound No. 135) having a melting point of from 193 to 195° C.

Compounds of the above formula (I) produced in Preparation Examples 1 to 7 and by methods in accordance with the above Preparation Methods 1 and 2 are shown in the following Tables 1 to 20.

TABLE 1

| Compound No. | Structural Formula | Physical Properties |
| --- | --- | --- |
| 1 | | m.p.: 219° C. |
| 2 | | m.p.: 220–226° C. |
| 3 | | m.p.: 211° C. |
| 4 | | m.p.: 173° C. |
| 5 | | m.p.: 186–188° C. |

TABLE 1-continued

| Compound No. | Structural Formula | Physical Properties |
| --- | --- | --- |
| 6 | 3-chloro-N-[3-chloro-4-(5-trifluoromethylpyridin-2-yloxy)phenyl]benzamide | m.p.: 160–161° C. |
| 7 | 3-trifluoromethyl-N-[3-chloro-4-(5-trifluoromethylpyridin-2-yloxy)phenyl]benzamide | m.p.: 127–129° C. |
| 8 | 4-trifluoromethyl-N-[3-chloro-4-(5-trifluoromethylpyridin-2-yloxy)phenyl]benzamide | m.p.: 154–155° C. |
| 9 | 3,4-dimethoxy-N-[3-chloro-4-(5-trifluoromethylpyridin-2-yloxy)phenyl]benzamide | m.p.: 152–154° C. |

TABLE 2

| Compound No. | Structural Formula | Physical Propertiees |
| --- | --- | --- |
| 10 | 3-methoxy-N-[3-chloro-4-(5-trifluoromethylpyridin-2-yloxy)phenyl]benzamide | m.p.: 103–105° C. |
| 11 | 2,4-difluoro-N-[3-chloro-4-(5-trifluoromethylpyridin-2-yloxy)phenyl]benzamide | m.p.: 145–147° C. |

TABLE 2-continued
| Compound No. | Structural Formula | Physical Properties |
|---|---|---|
| 12 | 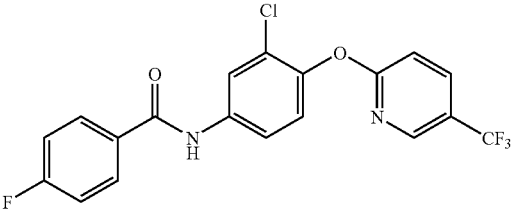 | m.p.: 174–176° C. |
| 13 | 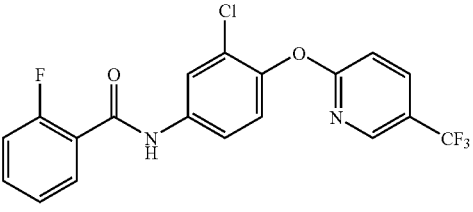 | m.p.: 141—143° C. |
| 14 | 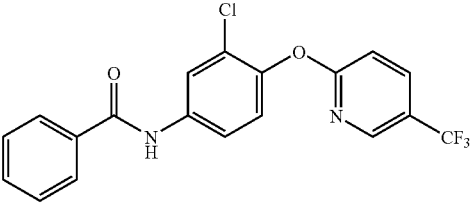 | m.p.: 170–172° C. |
| 15 | 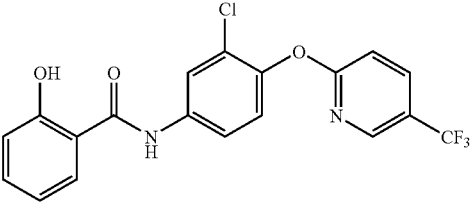 | m.p.: 165–167° C. |
| 16 | 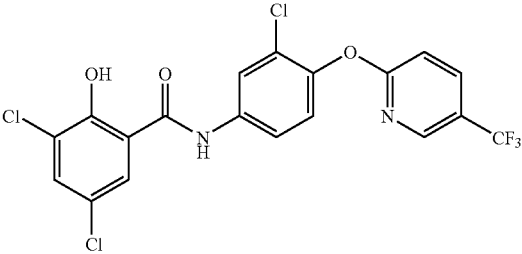 | m.p.: 176–178° C. |
| 17 | 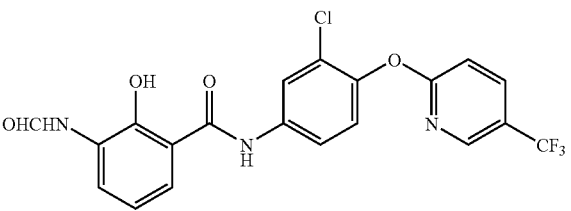 | m.p.: 159–161° C. |
| 18 | 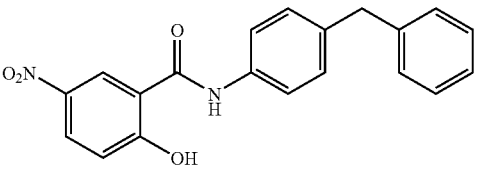 | m.p.: 211.5–214.4° C. |

TABLE 3

| Compound No. | Structural Formula | Physical Properties |
|---|---|---|
| 19 | 5-nitro-2-chloro-N-(2-methylphenyl)benzamide | m.p.: 207° C. |
| 20 | 5-nitro-2-chloro-N-(4-tert-butylphenyl)benzamide | m.p.: 182° C. |
| 21 | 5-nitro-2-chloro-N-(4-adamantylphenyl)benzamide | m.p.: 262° C. |
| 22 | 2-chloro-N-(4-adamantyl-2-methylphenyl)benzamide | m.p.: 154° C. |
| 23 | 3-nitro-N-(4-adamantyl-2-methylphenyl)benzamide | m.p.: 177° C. |
| 24 | 2,5-dichloro-N-(4-adamantyl-2-methylphenyl)benzenesulfonamide | m.p.: 200° C. |
| 25 | 2-chloro-N-(4-adamantyl-2-methylphenyl)benzenesulfonamide | m.p.: 200° C. |

TABLE 3-continued

| Compound No. | Structural Formula | Physical Properties |
| --- | --- | --- |
| 26 | 2-chloro-5-nitro-N-(2,4-dimethylphenyl)benzamide | m.p.: 206° C. |
| 27 | 2-chloro-5-nitro-N-(4-phenoxyphenyl)benzamide | m.p.: 128° C. |

TABLE 4

| Compound No. | Structural Formula | Physical Properties |
| --- | --- | --- |
| 28 | 2-chloro-5-nitro-N-(4-methoxyphenyl)benzamide | m.p.: 154° C. |
| 29 | 2-chloro-5-nitro-N-(4-methylthiophenyl)benzamide | m.p.: 162° C. |
| 30 | 2-chloro-5-nitro-N-(4-trifluoromethylphenyl)benzamide | m.p.: 176° C. |
| 31 | 2-chloro-5-nitro-N-[2-methyl-4-(4-trifluoromethylphenoxy)phenyl]benzamide | m.p.: 196° C. |
| 32 | 2-chloro-5-nitro-N-{4-[(5-trifluoromethylpyridin-2-yl)thio]phenyl}benzamide | m.p.: 189° C. |

TABLE 4-continued

| Compound No. | Structural Formula | Physical Properties |
|---|---|---|
| 33 | 2-chloro-5-nitro-N-(3-(trifluoromethyl)phenyl)benzamide | m.p.: 168° C. |
| 34 | methyl 3-((4-(adamantan-1-yl)-2-methylphenyl)carbamoyl)benzoate | m.p.: 184° C. |
| 35 | 3-((4-(adamantan-1-yl)-2-methylphenyl)carbamoyl)benzoic acid | m.p.: 232° C. |
| 36 | N-(4-(adamantan-1-yl)-2-methylphenyl)-2-methyl-5-nitrobenzamide | m.p.: 198° C. |

TABLE 5

| Compound No. | Structural Formula | Physical Properties |
|---|---|---|
| 37 | 2-chloro-5-nitro-N-(2-phenoxyphenyl)benzamide | m.p.: 110° C. |
| 38 | N-([1,1'-biphenyl]-2-yl)-2-chloro-5-nitrobenzamide | m.p.: 154° C. |
| 39 | 2-chloro-5-nitro-N-(2-(trifluoromethyl)phenyl)benzamide | m.p.: 146° C. |

TABLE 5-continued
| Compound No. | Structural Formula | Physical Properties |
|---|---|---|
| 40 | 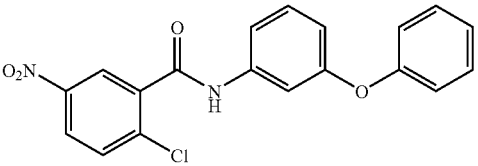 | m.p.: 103° C. |
| 41 | 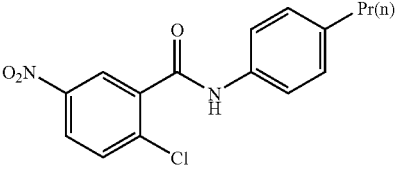 | m.p.: 147° C. |
| 42 | 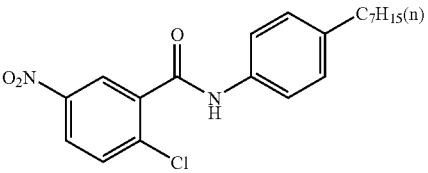 | m.p.: 131° C. |
| 43 | 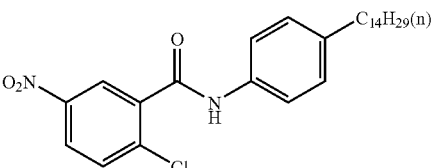 | m.p.: 121° C. |
| 44 | 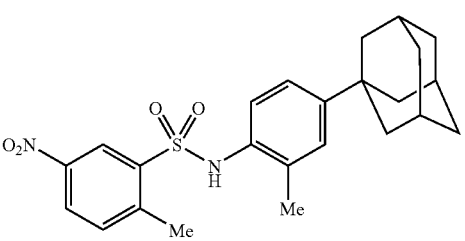 | m.p.: 241° C. |
| 45 | 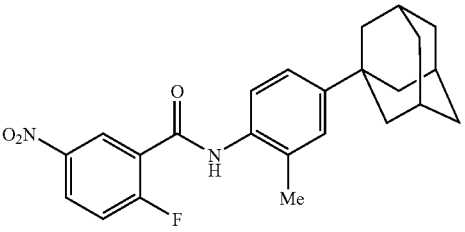 | m.p.: 198° C. |
TABLE 6
| Compound No. | Structural Formula | Physical Properties |
|---|---|---|
| 46 | 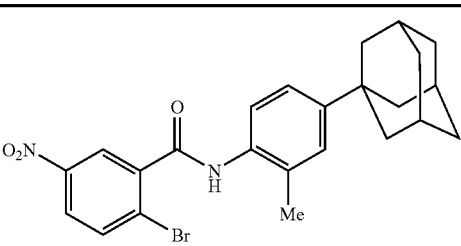 | m.p.: 229° C. |

TABLE 6-continued

| Compound No. | Structural Formula | Physical Properties |
| --- | --- | --- |
| 47 | 3-nitro-5-(methoxycarbonyl)-N-(4-adamantan-1-yl-2-methylphenyl)benzamide | m.p.: 178° C. |
| 48 | 2-chloro-5-nitro-N-(4-adamantan-1-yl-2-methylphenyl)benzenesulfonamide | m.p.: 238° C. |
| 49 | 2-chloro-5-nitro-N-(4-phenoxyphenyl)benzenesulfonamide | m.p.: 148° C. |
| 50 | 3-cyano-N-(4-adamantan-1-yl-2-methylphenyl)benzamide | m.p.: 83° C. |
| 51 | 2-chloro-5-nitro-N-(4-benzoylphenyl)benzamide | m.p.: 226° C. |
| 52 | 2,6-dimethoxy-3-nitro-N-(4-adamantan-1-yl-2-methylphenyl)benzamide | m.p.: 115° C. |

TABLE 6-continued
| Compound No. | Structural Formula | Physical Properties |
|---|---|---|
| 53 | 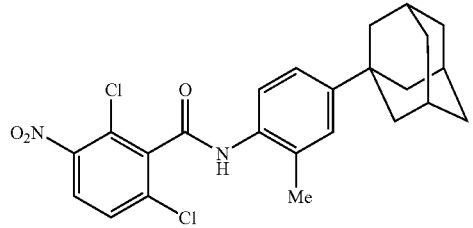 | m.p.: 224° C. |
| 54 | 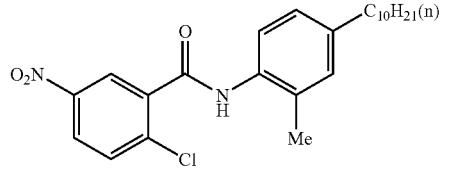 | m.p.: 128° C. |
TABLE 7
| Compound No. | Structural Formula | Physical Properties |
|---|---|---|
| 55 | 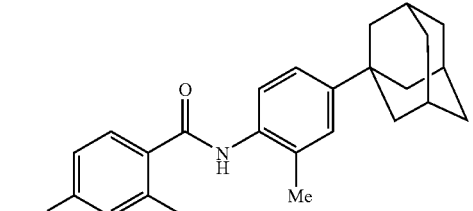 | m.p.: 200° C. |
| 56 | 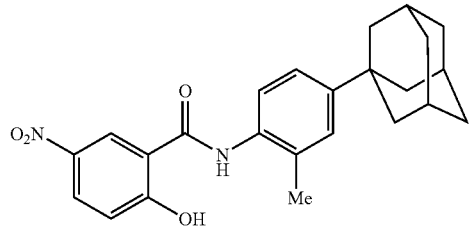 | m.p.: 131° C. |
| 57 | 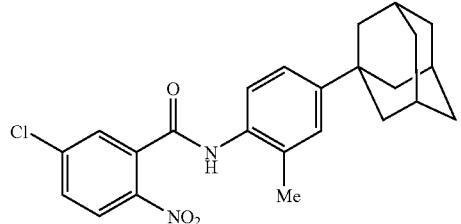 | m.p.: 233° C. |
| 58 | 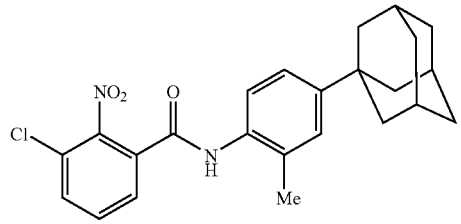 | m.p.: 256° C. |

TABLE 7-continued

| Compound No. | Structural Formula | Physical Properties |
|---|---|---|
| 59 | (structure) | m.p.: 174° C. |
| 60 | (structure) | m.p.: 222° C. |
| 61 | (structure) | m.p.: 198° C. |
| 62 | (structure) | m.p.: 111° C. |
| 63 | (structure) | m.p.: 198° C. |

TABLE 8

| Compound No. | Structural Formula | Physical Properties |
|---|---|---|
| 64 | (structure) | m.p.: 203° C. |
| 65 | (structure) | m.p.: 171° C. |

TABLE 8-continued

| Compound No. | Structural Formula | Physical Properties |
| --- | --- | --- |
| 66 | 2-Cl-5-O₂N-C₆H₃-C(O)-NH-C₆H₄-(4-morpholino) | m.p.: 195° C. |
| 67 | 2-Cl-5-O₂N-C₆H₃-C(O)-NH-C₆H₄-N=N-C₆H₅ | m.p.: 187° C. |
| 68 | 2-Cl-5-MeS-C₆H₃-C(O)-NH-(2-Me-4-(1-adamantyl)-C₆H₃) | m.p.: 65° C. |
| 69 | 2-Cl-5-O₂N-C₆H₃-C(O)-NH-C₆H₄-S-C₆H₅ | m.p.: 180–183° C. |
| 70 | 2-Cl-5-F₃C-C₆H₃-C(O)-NH-(2-Me-4-(1-adamantyl)-C₆H₃) | m.p.: 69° C. |
| 71 | 2-Cl-C₆H₄-C(O)-NH-(3-Cl-4-((5-CF₃-pyridin-2-yl)oxy)-C₆H₃) | m.p.: 168–169° C. |
| 72 | 3-Cl-4-((5-CF₃-pyridin-2-yl)oxy)-C₆H₃-C(O)-NH-(3-Cl-4-((5-CF₃-pyridin-2-yl)oxy)-C₆H₃) | m.p.: 206–209° C. |

TABLE 9

| Compound No. | Structural Formula | Physical Properties |
| --- | --- | --- |
| 73 | 2-chloro-4-nitro-N-(2,4-dimethylphenyl)benzamide | m.p.: 181–183° C. |
| 74 | 4-nitro-N-(4-(1-adamantyl)-2-methylphenyl)benzamide | m.p. 289–290° C. |
| 75 | 2-chloro-5-(methylsulfonyl)-N-(4-(1-adamantyl)-2-methylphenyl)benzamide | m.p.: 96–100° C. |
| 76 | 2-chloro-5-cyano-N-(4-(1-adamantyl)-2-methylphenyl)benzamide | m.p.: 184–187° C. |
| 77 | 2-chloro-5-nitro-N-(4-benzyloxyphenyl)benzamide | m.p.: 176–178° C. |
| 78 | 2-chloro-5-nitro-N-(4-benzylthiophenyl)benzamide | m.p.: 156–157° C. |

TABLE 9-continued

| Compound No. | Structural Formula | Physical Properties |
| --- | --- | --- |
| 79 | | m.p.: 176–180° C. |
| 80 | | m.p.: 171° C. |
| 81 | | |

TABLE 10

| Compound No. | Structural Formula | Physical Properties |
| --- | --- | --- |
| 82 | | m.p.: 207–208° C. |
| 83 | | m.p.: 203–206° C. |
| 84 | | |

TABLE 10-continued

| Compound No. | Structural Formula | Physical Properties |
| --- | --- | --- |
| 85 | | m.p.: 143° C. |
| 86 | | m.p.: 209–212° C. |
| 87 | | m.p.: 229–231° C. |
| 88 | | m.p.: 221° C. |
| 89 | | m.p.: 168° C. |
| 90 | | m.p.: 224–226° C. |

TABLE 11

| Compound No. | Structural Formula | Physical Properties |
| --- | --- | --- |
| 91 | | m.p.: 219–221° C. |

TABLE 11-continued
| Compound No. | Structural Formula | Physical Properties |
|---|---|---|
| 92 | 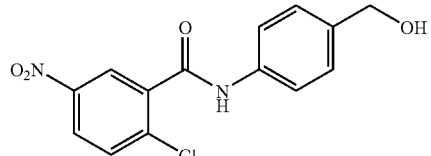 | m.p.: 201–204° C. |
| 93 | 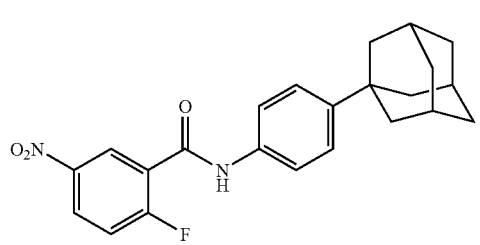 | m.p.: 224–228° C. |
| 94 | 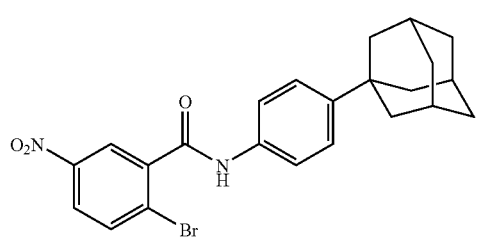 | m.p.: 273–275° C. |
| 95 | 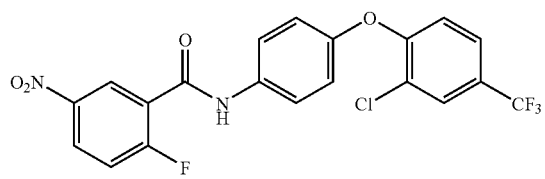 | 129–131° C. |
| 96 | 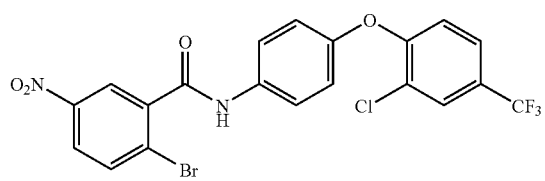 | m.p.: 167–172° C. |
| 97 | 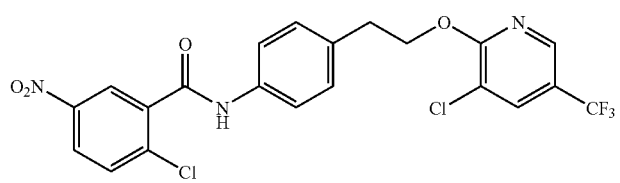 | m.p.: 131–134° C. |
| 98 | 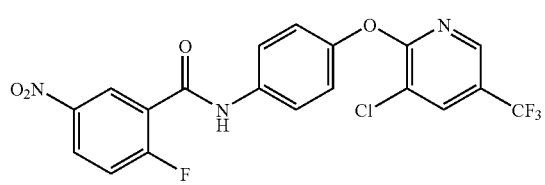 | m.p.: 168–170° C. |

TABLE 11-continued
| Compound No. | Structural Formula | Physical Properties |
|---|---|---|
| 99 | 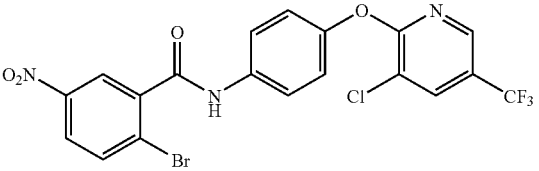 | m.p.: 191–195° C. |
TABLE 12
| Compound No. | Structural Formula | Physical Properties |
|---|---|---|
| 100 | 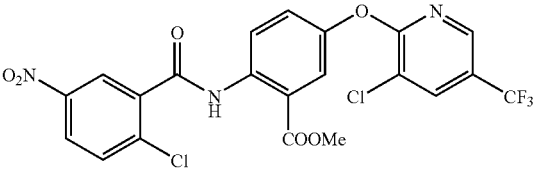 | m.p.: 154–158° C. |
| 101 | 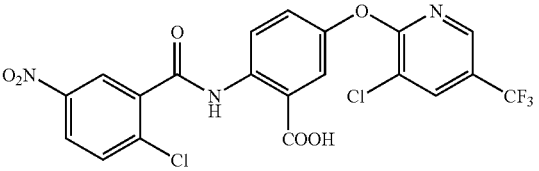 | m.p.: 240–245° C. |
| 102 | 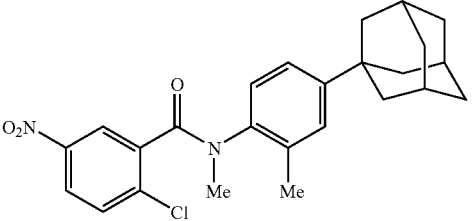 | Oily matter |
| 103 | 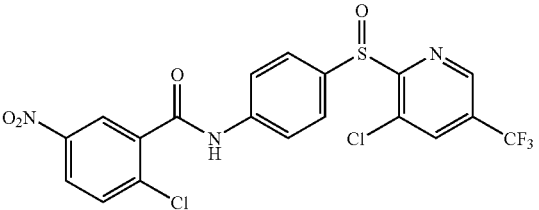 | Amorphous solid |
| 104 | 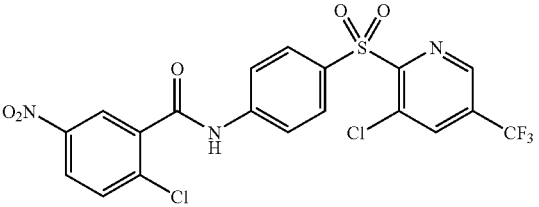 | Amorphous solid |
| 105 | 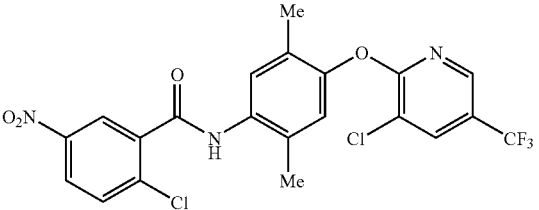 | m.p.: 296–298° C. |

TABLE 12-continued

| Compound No. | Structural Formula | Physical Properties |
|---|---|---|
| 106 | (structure with Me substituent) | m.p.: 230–232° C. |
| 107 | (structure with COOMe substituent) | m.p.: 226–229° C. |
| 108 | (structure with NO₂ substituent) | m.p.: 233–236° C. |

TABLE 13

| Compound No. | Structural Formula | Physical Properties |
|---|---|---|
| 109 | (structure with OMe substituent) | m.p.: 190–193° C. |
| 110 | (structure with adamantylmethoxy group) | m.p.: 175–180° C. |
| 111 | (structure with adamantyloxy group) | m.p.: 178–180° C. |

TABLE 13-continued

| Compound No. | Structural Formula | Physical Properties |
| --- | --- | --- |
| 112 | (structure) | m.p.: 189–191° C. |
| 113 | (structure) | m.p.: 222–225° C. |
| 114 | (structure) | Amorphous solid |
| 115 | (structure) | Solid material |
| 116 | (structure) | m.p.: 239–244° C. |
| 117 | (structure) | m.p.: 233–236° C. |

TABLE 14

| Compound No. | Structural Formula | Physical Properties |
| --- | --- | --- |
| 118 | [structure: 5-cyano-2-chloro-benzamide linked via NH to 3-methyl-4-(3-chloro-5-trifluoromethyl-pyridin-2-yloxy)phenyl] | m.p.: 221–223° C. |
| 119 | [structure: 5-nitro-2-fluoro-benzamide linked via NH to 3-methyl-4-(3-chloro-5-trifluoromethyl-pyridin-2-yloxy)phenyl] | m.p.: 179–181° C. |
| 120 | [structure: 5-nitro-2-bromo-benzamide linked via NH to 3-methyl-4-(3-chloro-5-trifluoromethyl-pyridin-2-yloxy)phenyl] | m.p.: 246–248° C. |
| 121 | [structure: 5-nitro-2-chloro-benzamide linked via NH to 3-amino-4-(3-chloro-5-trifluoromethyl-pyridin-2-yloxy)phenyl] | m.p.: 235–237° C. |
| 122 | [structure: 5-nitro-2-chloro-benzamide linked via NH to 3-cyano-4-(3-chloro-5-trifluoromethyl-pyridin-2-yloxy)phenyl] | m.p.: 194–198° C. |
| 123 | [structure: 5-nitro-2-chloro-benzamide linked via NH to 6-(adamantyloxy)pyridin-3-yl] | m.p.: 98–105° C. |
| 124 | [structure: 5-nitro-2-chloro-benzamide linked via NH to 6-(2-adamantyloxy)pyridin-3-yl] | Amorphous solid |

TABLE 14-continued

| Compound No. | Structural Formula | Physical Properties |
|---|---|---|
| 125 | | m.p.: 203–205° C. |
| 126 | | m.p.: 194–197° C. |

TABLE 15

| Compound No. | Structural Formula | Physical Properties |
|---|---|---|
| 127 | | m.p.: 165–167° C. |
| 128 | | m.p.: 208–213° C. |
| 129 | | m.p.: 273–276° C. |
| 130 | | m.p.: 235–237° C. |

TABLE 15-continued
| Compound No. | Structural Formula | Physical Properties |
|---|---|---|
| 131 | | m.p.: 194–198° C. |
| 132 | | m.p.: 215–218° C. |
| 133 | | m.p.: 212–216° C. |
| 134 | | Amorphous solid |
| 135 | | m.p.: 193–195° C. |
TABLE 16
| Compound No. | Structural Formula | Physical Properties |
|---|---|---|
| 136 | 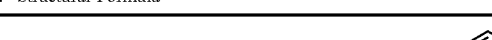 | m.p.: 178–181° C. |

TABLE 16-continued

| Compound No. | Structural Formula | Physical Properties |
|---|---|---|
| 137 | (structure) | m.p.: 252–258° C. |
| 138 | (structure) | m.p.: 146–150° C. |
| 139 | (structure) | m.p.: 225–229° C. |
| 140 | (structure) | m.p.: 242–244° C. |
| 141 | (structure) | m.p.: 217–221° C. |
| 142 | (structure) | m.p.: 140–147° C. |
| 143 | (structure) | m.p.: 221–227° C. |

TABLE 16-continued

| Compound No. | Structural Formula | Physical Properties |
| --- | --- | --- |
| 144 | (structure) | m.p.: 116° C. |

TABLE 17

| Compound No. | Structural Formula | Physical Properties |
| --- | --- | --- |
| 145 | (structure) | m.p.: 165–172° C. |
| 146 | (structure) | m.p.: 235–237° C. |
| 147 | (structure) | Amorphous solid |
| 148 | (structure) | m.p.: 189–192° C. |
| 149 | (structure) | |

TABLE 17-continued

| Compound No. | Structural Formula | Physical Properties |
|---|---|---|
| 150 | | |
| 151 | | |
| 152 | | |
| 153 | | |

TABLE 18

| Compound No. | Structural Formula | Physical Properties |
|---|---|---|
| 154 | | |
| 155 | | |

TABLE 18-continued
| Compound No. | Structural Formula | Physical Properties |
|---|---|---|
| 156 | 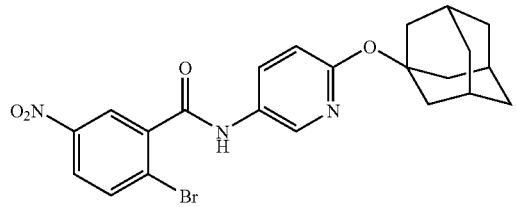 | |
| 157 | 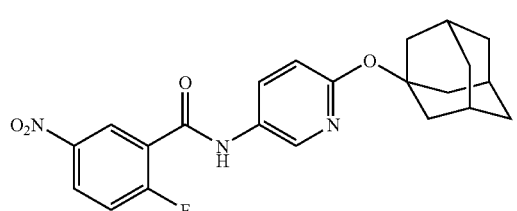 | |
| 158 | 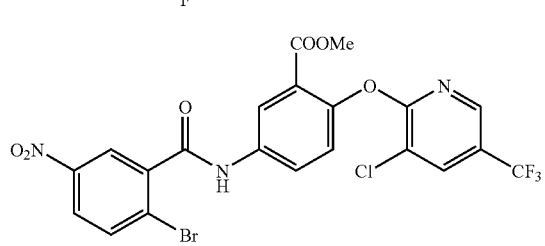 | |
| 159 | 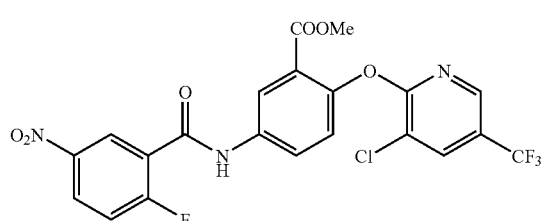 | |
| 160 | 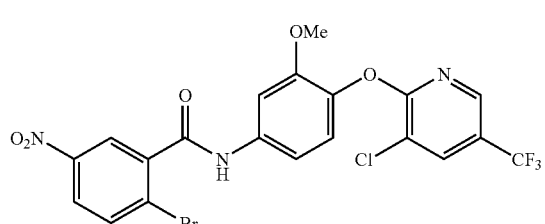 | |
| 161 | 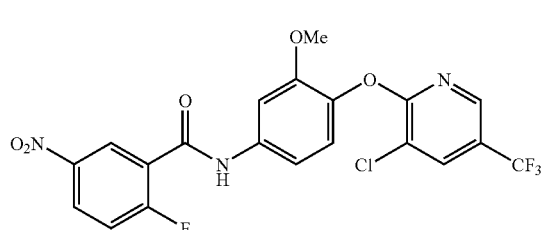 | |
| 162 | 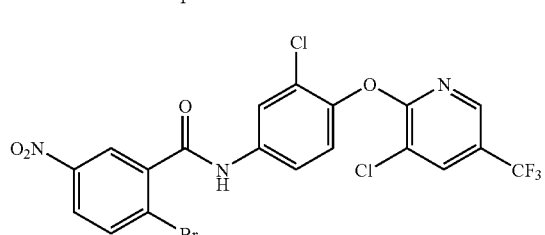 | |

TABLE 19

| Compound No. | Structural Formula | Physical Properties |
| --- | --- | --- |
| 163 | | |
| 164 | | |
| 165 | | |
| 166 | | |
| 167 | | |
| 168 | | |
| 169 | | |

TABLE 19-continued
| Compound No. | Structural Formula | Physical Properties |
|---|---|---|
| 170 | 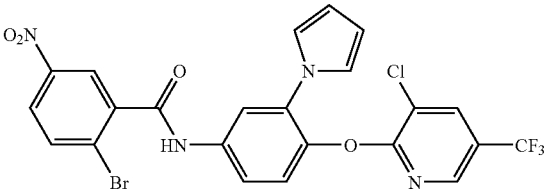 | |
| 171 | 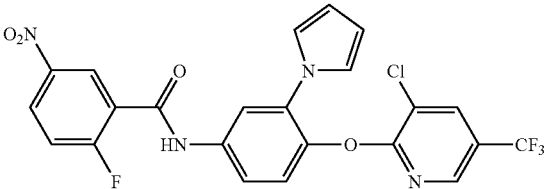 | |
TABLE 20
| Compound No. | Structural Formula | Physical Properties |
|---|---|---|
| 172 | 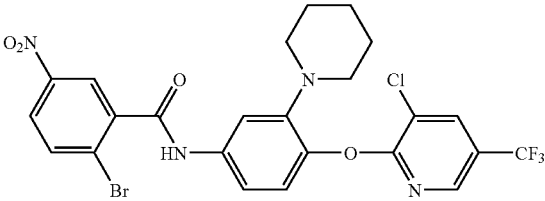 | |
| 173 | 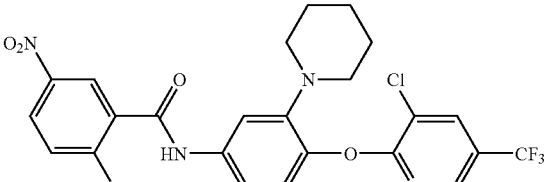 | |
| 174 | 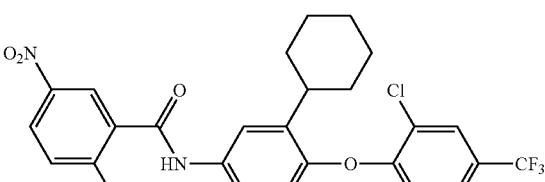 | |
| 175 | 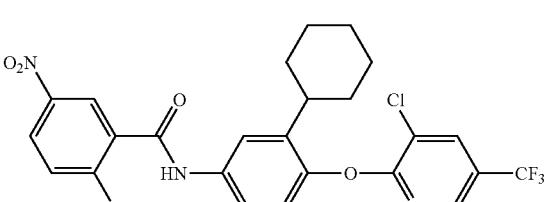 | |

TABLE 20-continued

| Compound No. | Structural Formula | Physical Properties |
| --- | --- | --- |
| 176 | | |
| 177 | | |
| 178 | | |
| 179 | | |

Test Example (Test for Evaluation of Cytokine Production Inhibitory Effect)

Murine spleen cells were treated with anti-mouse CD3 antibody and IL-2 to induce cytokine production. The test compounds were added to the cytokine production system to evaluate their inhibitory effect. Namely, anti-mouse CD3 antibody adjusted to from 10 to 20 μg/ml with borate buffered physiological saline (pH 8.5) was pipetted into a 96-well cell culture plate in an amount of 50 μl/well and left to stand at 4° C. for 18 hours. The unreacted solution was removed, washing with Hank's buffer solution was carried out once, and IL-2 adjusted to 10 ng/ml with a RPMI liquid containing 10% fetal bovine serum (FCS) was pipetted in an amount of 50 μl/well. For the negative control group, a solution alone without anti-CD3 antibody nor IL-2 was applied. Then, the diluted solution of each of the test compounds (concentration: 100 ppm unless otherwise specified) was pipetted in an amount of 50 μl/well, and a cell suspension of $1 \times 10^7$ cells/ml, prepared from spleen of Balb/c mice (female, 7 to 10 week old) was pipetted thereinto in an amount of 100 μl/well. After cultivation in an incubator (37° C., 5% carbon dioxide gas) for from 40 to 48 hours, the culture supernatant was recovered to measure the cytokine production amount by ELISA method.

With respect to interleukin 5 (IL-5) as a typical Th2 type cytokine and interferon γ (IFN-γ) as a typical Th1 type cytokine, measurements were carried out by the following methods, respectively. Namely, quantitative determination of IL-5 was carried out by the following ELISA method. First, rat anti-mouse IL-5 antibody (Endogen Code No. MM-550C) as a primary antibody was diluted with carbonate buffer solution (pH 9.5) to 1 μg/ml, and spread in a 96 well plate (IWAKI, Code No. 3860-096) in an amount of 50 μl/well for coating at 4° C. overnight (16 to 24 hours). Then, the plate was subjected to blocking at 37° C. for 2 hours by phosphate buffered physiological saline containing 10% FCS (pH 7.2) (blocking buffer solution) (250 μl/well). The plate was washed with PBS (washing buffer) containing 0.05% Tween 20 (Nacalai Tesque, Code No. 281-51) four times, and a diluted liquid of the culture supernatant was spread in an amount of 50 μl/well, followed by incubation at room temperature for 1 hour. For preparation of a standard line, recombinant mouse IL-5 (R&D systems, Code No. 405-ML) was employed. The plate was washed with a washing buffer four times, and biotin-labeled rat anti-mouse IL-5 antibody (Pharmingen, Code No. 18062D) as a secondary antibody diluted to 0.5 μg/ml with a blocking buffer containing 0.05% Tween 20 was added thereto (50 μl/well), followed by incubation at room temperature for 1 hour. The plate was washed with a washing buffer four times, strept avidin-labeled peroxidase (ProZyme, Code No. CJ30H001) diluted 800 times with a blocking buffer containing 0.05% Tween 20 was added thereto (50 μl/well), followed by reaction at room temperature for 15 minutes. The plate was washed with a washing buffer four times, and a TNB substrate solution (SIGMA, Code No. T-8665) was added thereto in an amount of 100 μl/well for color developing for from 10 to 20 minutes. A 1M sulfuric acid solution was added thereto in an amount of 100 μl/well to terminate the reaction, and absorption (wavelength 450 nm) was measured by means of micro plate reader (SPECTRA max, Wako Pure Chemicals Industries, Ltd.). Quantitative determination of IFN-γ was carried out in the same manner as the measurement of IL-5, employing rat anti-mouse IFN-γ antibody (Pharmingen, Code No. 18181D) and biotin labeled rat anti-mouse IFN-γ antibody (Pharmingen, Code NO. 18112D), as a primary antibody and a secondary antibody, respectively. For preparation of a standard line, recombinant mouse IFN-γ (GENZYME, Code No. 3485) was employed. The experiment was carried out in duplicate, and the average of the cytokine production amount was obtained. From the average value, the inhibitory ratio (%) was obtained from the following formula, and the results are shown in Tables 21 to 24. With respect to the inhibitory ratio in a case where the concentration of the test compound was not 100 ppm, the concentration of the test compound is shown in ( ) after each inhibitory ratio.

Inhibitory ratio (%)={1−(T−N)/(P−N)}×100

T: average value of the test compound group, N: average value of the negative control group, and P: average value of the positive control group.

TABLE 21

| No. | IL-5 production inhibitory ratio (%) | IFN-γ production inhibitory ratio (%) | No. | IL-5 production inhibitory ratio (%) | IFN-γ production inhibitory ratio (%) |
|---|---|---|---|---|---|
| 1 | 96 | 90 | 5 | 76 | 83 |
| 2 | 74 (2 ppm) | 84 (2 ppm) | 6 | 100 | 100 |
| 3 | 79 | 92 | 7 | 100 | 100 |
| 4 | 47 | 76 | 8 | 58 (10 ppm) | 67 (10 ppm) |

TABLE 22

| No. | IL-5 production inhibitory ratio (%) | IFN-γ production inhibitory ratio (%) | No. | IL-5 production inhibitory ratio (%) | IFN-γ production inhibitory ratio (%) |
|---|---|---|---|---|---|
| 9 | 96 | 100 | 32 | 99 | 98 |
| 10 | 100 | 100 | 33 | 100 | 100 |
| 11 | 37 | | 34 | 88 | 97 |
| 12 | 33 | | 35 | 100 | 100 |
| 13 | 36 | | 36 | 81 | 85 |
| 14 | 46 | | 37 | 97 | 100 |
| 15 | 99 | 100 | 38 | 86 | 93 |
| 16 | 100 | | 39 | 97 | 100 |
| 17 | 100 | 100 | 40 | 100 | 100 |
| 18 | 100 | 100 | 41 | 99 | 100 |
| 19 | 96 | 88 | 42 | 56 | 81 |
| 20 | 100 | 100 | 43 | 98 | 98 |
| 21 | 96 | 89 | 44 | 93 | 100 |
| 22 | 100 | 100 | 45 | 99 | 99 |
| 23 | 100 | 100 | 46 | 100 | 98 |
| 24 | 100 | | 47 | 89 | 95 |
| 25 | 89 | 93 | 48 | 100 | 100 |
| 26 | 82 | 30 | 49 | 100 | 100 |
| 27 | 96 | 99 | 50 | 95 | 98 |
| 28 | 100 | 100 | 51 | 99 | 100 |
| 29 | 98 | 100 | 52 | 75 | 96 |
| 30 | 100 | 100 | 53 | 94 | 93 |
| 31 | 62 | 63 | 54 | 62 | 78 |

TABLE 23

| No. | IL-5 production inhibitory ratio (%) | IFN-γ production inhibitory ratio (%) | No. | IL-5 production inhibitory ratio (%) | IFN-γ production inhibitory ratio (%) |
|---|---|---|---|---|---|
| 55 | 96 | 100 | 77 | 74 | 50 |
| 56 | 100 | 100 | 78 | 78 | 91 |
| 57 | 90 | 98 | 79 | 62 | 90 |
| 58 | 97 | 96 | 80 | 100 | 100 |
| 59 | 100 | 100 | 82 | 90 | 99 |
| 60 | 96 | 93 | 83 | 90 | 76 |
| 61 | 79 | 89 | 85 | 91 | 86 |
| 62 | 100 | 100 | 86 | 87 | 29 |
| 63 | 100 | 100 | 87 | 100 | 100 |
| 64 | 98 | 99 | 88 | 72 | 17 |
| 65 | 100 | 100 | 89 | 87 | 99 |
| 66 | 95 | 91 | 90 | 100 | 100 |
| 67 | 99 | 100 | 91 | 53 | 1 |
| 68 | 92 | 99 | 92 | 99 | 100 |
| 69 | 100 | 100 | 93 | 100 | 100 |
| 70 | 98 | 99 | 94 | 85 | 53 |
| 71 | 89 | | 95 | 100 | 100 |
| 72 | 51 | | 96 | 100 | 100 |
| 73 | 64 | 28 | 97 | 77 | 84 |
| 74 | 43 | 10 | 98 | 96 | 99 |
| 75 | 100 | 100 | 99 | 100 | 89 |
| 76 | 96 | 96 | 100 | 92 | 93 |

TABLE 24

| No. | IL-5 production inhibitory ratio (%) | IFN-γ production inhibitory ratio (%) | No. | IL-5 production inhibitory ratio (%) | IFN-γ production inhibitory ratio (%) |
|---|---|---|---|---|---|
| 101 | 100 | 100 | 125 | 100 | 100 |
| 102 | 100 | 100 | 126 | 100 | 100 |
| 103 | 100 | 100 | 127 | 100 | 100 |
| 104 | 100 | 100 | 128 | 96 | 93 |
| 105 | 55 | 25 | 129 | 86 | 67 |
| 106 | 83 | 96 | 130 | 100 | 99 |
| 107 | 99 | 97 | 131 | 100 | 100 |
| 108 | 100 | 100 | 132 | 99 | 100 |
| 109 | 100 | 95 | 133 | 99 | 100 |
| 110 | 99 | 100 | 134 | 97 | 98 |
| 111 | 99 | 99 | 135 | 62 | 33 |
| 112 | 100 | 100 | 136 | 98 | 100 |
| 113 | 96 | 97 | 137 | 98 | 98 |
| 114 | 100 | 100 | 138 | 99 | 100 |
| 115 | 100 | 100 | 139 | 89 | 50 |
| 116 | 100 | 99 | 140 | 100 | 100 |
| 117 | 100 | 100 | 141 | 100 | 100 |
| 118 | 78 | 47 | 142 | 95 | 99 |
| 119 | 100 | 99 | 143 | 97 | 100 |
| 120 | 84 | 35 | 144 | 99 | 100 |
| 121 | 97 | 100 | 145 | 100 | 100 |
| 122 | 100 | 100 | 146 | 62 | 43 |
| 123 | 100 | 100 | 147 | 99 | 100 |
| 124 | 100 | 100 | 148 | 94 | 81 |

INDUSTRIAL APPLICABILITY

The present invention provides cytokine production inhibitors useful as preventive or therapeutic medicines for diseases accompanied by hyperactivated immune functions.

The invention claimed is:
1. An aniline derivative of the formula (I') or a salt thereof, said derivative and salt having cytokine production inhibitor activity:

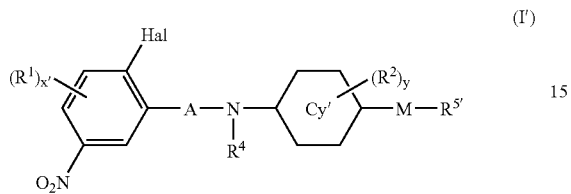

wherein A is CO or $SO_2$; each of $R^1$ and $R^2$ which are independent of each other, is a halogen atom, a cyano group, a nitro group, an alkyl group which may be substituted, an alkenyl group which may be substituted, an alkynyl group which may be substituted, a cycloalkyl group which may be substituted, a cycloalkenyl group which may be substituted, an aryl group which may be substituted, an amino group which may be substituted or a —B-Q group (wherein B is O, CO, COO, OCO, S, SO or $SO_2$; Q is a hydrogen atom, an alkyl group which may be substituted, an alkenyl group which may be substituted, an alkynyl group which may be substituted, a cycloalkyl group which may be substituted, a cycloalkenyl group which may be substituted, an aryl group which may be substituted, or an amino group which may be substituted); wherein the substituent of each of the alkyl group which may be substituted, the alkenyl group which may be substituted and the alkynyl group which may be substituted, is a halogen atom, a hydroxyl group, a mercapto group, an alkoxy group, an alkylthio group, an alkenyloxy group, an alkenylthio group, an alkynyloxy group, an alkynylthio group, a cycloalkyl group, a cycloalkenyl group, a cycloalkoxy group, a cycloalkylthio group, a cycloalkenyloxy group, a cycloalkenylthio group, an alkoxycarbonyl group, an alkylcarbonyl group, an alkylcarbonyloxy group, an alkenyloxycarbonyl group, an alkenylcarbonyl group, an alkenylcarbonyloxy group, an alkynyloxycarbonyl group, an alkynylcarbonyl group, an alkynylcarbonyloxy group, a cycloalkoxycarbonyl group, a cycloalkylcarbonyl group, a cycloalkylcarbonyloxy group, a cycloalkenyloxycarbonyl group, a cycloalkenylcarbonyl group, a cycloalkenylcarbonyloxy group, an aryl group, an aryloxy group, an arylthio group, an aryloxycarbonyl group, an arylcarbonyl group, an arylcarbonyloxy group, an amino group, a cyano group, a nitro group, a carboxyl group, an aminocarbonyl group, an alkylsulfonyl group, an alkenylsulfonyl group, an alkynylsulfonyl group, a cycloalkylsulfonyl group, a cycloalkenylsulfonyl group, an arylsulfonyl group, or an aminosulfonyl group; the substituent of each of the cycloalkyl group which may be substituted, the cycloalkenyl group which may be substituted, and the aryl group which may be substituted, is a halogen atom, a hydroxyl group, a mercapto group, an alkyl group, an alkenyl group, an alkynyl group, an alkoxy group, an alkylthio group, an alkenyloxy group, an alkenylthio group, an alkynyloxy group, an alkynylthio group, a cycloalkyl group, a cycloalkenyl group, a cycloalkoxy group, a cycloalkylthio group, a cycloalkenyloxy group, a cycloalkenylthio group, an alkoxycarbonyl group, an alkylcarbonyl group, an alkylcarbonyloxy group, an alkenyloxycarbonyl group, an alkenylcarbonyl group, an alkenylcarbonyloxy group, an alkynyloxycarbonyl group, an alkynylcarbonyl group, an alkynylcarbonyloxy group, a cycloalkoxycarbonyl group, a cycloalkylcarbonyl group, a cycloalkylcarbonyloxy group, a cycloalkenyloxycarbonyl group, a cycloalkenylcarbonyl group, a cycloalkenylcarbonyloxy group, an aryl group, an aryloxy group, an arylthio group, an aryloxycarbonyl group, an arylcarbonyl group, an arylcarbonyloxy group, an amino group, a cyano group, a nitro group, a carboxyl group, an aminocarbonyl group, an alkylsulfonyl group, an alkenylsulfonyl group, an alkynylsulfonyl group, a cycloalkylsulfonyl group, a cycloalkenylsulfonyl group, an arylsulfonyl group, or an aminosulfonyl group; the substituent of the amino group which may be substituted is a hydroxyl group, an alkyl group, an alkenyl group, an alkynyl group, an alkoxy group, an alkenyloxy group, an alkynyloxy group, a cycloalkyl group, a cycloalkenyl group, a cycloalkoxy group, a cycloalkenyloxy group, an alkoxycarbonyl group, an alkylcarbonyl group, an alkenyloxycarbonyl group, an alkenylcarbonyl group, an alkynyloxycarbonyl group, an alkynylcarbonyl group, a cycloalkoxycarbonyl group, a cycloalkylcarbonyl group, a cycloalkenyloxycarbonyl group, a cycloalkenylcarbonyl group, an aryl group, an aryloxy group, an aryloxycarbonyl group, an arylcarbonyl group, an aminocarbonyl group, an alkylsulfonyl group, an alkenylsulfonyl group, an alkynylsulfonyl group, a cycloalkylsulfonyl group, a cycloalkenylsulfonyl group, an arylsulfonyl group, or an aminosulfonyl group; $R^4$ is a hydrogen atom or an alkyl group; y is an integer of from 0 to 4; Hal is a halogen atom; Cy' is a phenyl group M is O, S, a $NR^6$ group (wherein $R^6$ is a hydrogen atom or an alkyl group), —$OCH_2$—, —$OCH_2CH_2$—, —$CH_2O$—, —$CH_2CH_2O$—, —$SCH_2$—, —$SCH_2CH_2$—, —$CH_2S$—, —$CH_2CH_2S$—or a single bond; $R^{5'}$ a pyridyl group which may be substituted with at least one substituent selected from the group consisting of a halogen atom, a hydroxyl group, a mercapto group, an alkyl group, a haloalkyl group, an alkenyl group, an alkynyl group, an alkoxy group, an alkylthio group, an alkenyloxy group, an alkenylthio group, an alkynyloxy group, an alkynylthio group, a cycloalkyl group, a cycloalkenyl group, a cycloalkoxy group, a cycloalkylthio group, a cycloalkenyloxy group, a cycloalkenylthio group, an alkoxycarbonyl group, an alkylcarbonyl group, an alkylcarbonyloxy group, an alkenyloxycarbonyl group, an alkenylcarbonyl group, an alkenylcarbonyloxy group, an alkynyloxycarbonyl group, an alkynylcarbonyl group, an alkynylcarbonyloxy group, a cycloalkoxycarbonyl group, a cycloalkylcarbonyl group, a cycloalkylcarbonyloxy group, a cycloalkenyloxycarbonyl group, a cycloalkenylcarbonyl group, a cycloalkenylcarbonyloxy group, an aryl group, an aryloxy group, an arylthio group, an aryloxycarbonyl group, an arylcarbonyl group, an arylcarbonyloxy group, an amino group, a cyano group, a nitro group, a carboxyl group, an aminocarbonyl group, an alkylsulfonyl group, an alkenylsulfonyl group, an alkynylsulfonyl group, a cycloalkylsulfonyl group, a cycloalkenylsulfonyl group, an arylsulfonyl group, and an aminosulfonyl group; or $R^{5'}$ is an adamantyl group; x' is an integer of from 0 to 3.

2. The aniline derivative or a salt thereof according to claim 1, wherein A is CO.

3. The aniline derivative or a salt thereof according to claim 1, wherein A is CO, and $R^{5'}$ is a pyridyl group which may be substituted.

4. The aniline derivative or a salt thereof according to claim 1, wherein A is CO, and $R^{5'}$ is a pyridyl group substituted with a haloalkyl group (provided that the pyridyl group may be substituted with at least one substituent selected from the group consisting of a halogen atom, a hydroxyl group, a mercapto group, an alkyl group, an alkenyl group, an alkynyl group, an alkoxy group, an alkylthio group, an alkenyloxy group, an alkenylthio group, an alkynyloxy group, an alkynylthio group, cycloalkyl group, a cycloalkenyl group, a cycloalkoxy group, a cycloalkylthio group, a cycloalkenyloxy group, a cycloalkenylthio group, an alkoxycarbonyl group, an alkylcarbonyl group, an alkylcarbonyloxy group, an alkenyloxycarbonyl group, an alkenylcarbonyl group, an alkenylcarbonyloxy group, an alkynyloxycarbonyl group, an alkynylcarbonyl group, an alkynylcarbonyloxy group, a cycloalkoxycarbonyl group, a cycloalkylcarbonyl group, a cycloalkylcarbonyloxy group, a cycloalkenyloxycarbonyl group, a cycloalkenylcarbonyl group, a cycloalkenylcarbonyloxy group, an aryl group, an aryloxy group, an arylthio group, an aryloxycarbonyl group, an arylcarbonyl group, an arylcarbonyloxy group, an amino group, a cyano group, a nitro group, a carboxyl group, an aminocarbonyl group, an alkylsulfonyl group, an alkenylsulfonyl group, an alkynylsulfonyl group, a cycloalkylsulfonyl group, a cycloalkenylsulfonyl group, an arylsulfonyl group, and an aminosulfonyl group).

5. The aniline derivative or a salt thereof according to claim 1, wherein A is CO, and $R^{5'}$ is a 3-chloro-5-trifluoromethyl-2-pyridyl group.

* * * * *